(12) United States Patent
Excoffon et al.

(10) Patent No.: US 10,736,971 B2
(45) Date of Patent: Aug. 11, 2020

(54) PEPTIDE-BASED MOLECULES FOR MODULATING CAR EXPRESSION OR ACCESSIBILITY AND USES THEREOF

(71) Applicant: Wright State University, Dayton, OH (US)

(72) Inventors: Katherine Julie Diane Ashbourne Excoffon, Dayton, OH (US); Priyanka Sharma, Beavercreek, OH (US)

(73) Assignee: WRIGHT STATE UNIVERSITYOH (US)

( * ) Notice: Subject to any disclaimer, the term of this patent is extended or adjusted under 35 U.S.C. 154(b) by 81 days.

(21) Appl. No.: 15/743,039

(22) PCT Filed: Jul. 9, 2016

(86) PCT No.: PCT/US2016/041671
§ 371 (c)(1),
(2) Date: Jan. 9, 2018

(87) PCT Pub. No.: WO2017/008067
PCT Pub. Date: Jan. 12, 2017

(65) Prior Publication Data
US 2018/0311369 A1   Nov. 1, 2018

Related U.S. Application Data

(60) Provisional application No. 62/190,461, filed on Jul. 9, 2015.

(51) Int. Cl.
*A61K 47/62* (2017.01)
*A61K 38/16* (2006.01)
*C07K 14/705* (2006.01)
*G01N 33/566* (2006.01)

(52) U.S. Cl.
CPC .............. *A61K 47/62* (2017.08); *A61K 38/16* (2013.01); *C07K 14/70596* (2013.01); *G01N 33/566* (2013.01); *C07K 2319/10* (2013.01); *C07K 2319/70* (2013.01); *C12N 2710/10311* (2013.01); *G01N 2333/075* (2013.01)

(58) Field of Classification Search
CPC .. A61K 47/62; A61K 38/16; C07K 14/70596; G91N 33/566
See application file for complete search history.

(56) References Cited

U.S. PATENT DOCUMENTS

| 2003/0096243 A1 | 5/2003 | Busa |
| 2003/0148264 A1 | 8/2003 | Held et al. |
| 2014/0056890 A1 | 2/2014 | Gurney et al. |

OTHER PUBLICATIONS

Kolawole, A. O., Sharma, P. et al., The PDZ1 and PDZ3 Domains of MAGI-1 Regulate the Eight-Exon Isoform of the Coxsackievirus and Adenovirus Receptor, J. Virology, Sep. 2012, pp. 9244-9254, vol. 86 No. 17, American Society for Microbiology.
Wegmann, F., Ebnet, K. et al., Endothelial adhesion molecule ESAM binds directly to the multidomain adaptor MAGI-1 and recruits it to cell contacts, Exp. Cell. Research, Aug. 2004, pp. 121-133, vol. 300, Elsevier.

*Primary Examiner* — Bao Q Li
(74) *Attorney, Agent, or Firm* — McNees Wallace & Nurick LLC

(57) ABSTRACT

Peptide-based molecules for modulating expression or accessibility to the coxsackievirus and adenovirus receptor (CAR) are disclosed. Cell-permeable peptide-based molecules having a PDZ-decoy domain or PDZ-binding domain are used to modulate the expression or accessibility of CAR molecules, thereby affecting the ability of viral molecules, or molecules containing viral sequences or proteins able to bind CAR, to enter host cells.

10 Claims, 19 Drawing Sheets

Specification includes a Sequence Listing.

A

B-

A

B

SEQUENCE LISTING

<160> NUMBER OF SEQ ID NOS: 48

<210> SEQ ID NO 1
<211> LENGTH: 13
<212> TYPE: PRT
<213> ORGANISM: Artificial Sequence
<220> FEATURE:
<223> OTHER INFORMATION: PEPTIDE WILL BE CREATED USING CONVENTIONA L
      MEANS

<400> SEQUENCE: 1

Gly Arg Lys Lys Arg Arg Gln Arg Arg Arg Pro Pro Gln
1               5                   10

<210> SEQ ID NO 2
<211> LENGTH: 16
<212> TYPE: PRT
<213> ORGANISM: Artificial Sequence
<220> FEATURE:
<223> OTHER INFORMATION: PEPTIDE WILL BE CREATED BY CONVENTIONAL MEANS

<400> SEQUENCE: 2

Arg Gln Ile Lys Ile Trp Phe Gln Asn Arg Arg Met Lys Trp Lys Lys

-continued

```
                1               5                  10                  15

<210> SEQ ID NO 3
<211> LENGTH: 9
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 3

Arg Arg Arg Arg Arg Arg Arg Arg Arg
1               5

<210> SEQ ID NO 4
<211> LENGTH: 9
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 4

Ala Lys Ala Ala Arg Gln Ala Ala Arg
1               5

<210> SEQ ID NO 5
<211> LENGTH: 33
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 5

Asp Ala Ala Thr Ala Thr Arg Gly Arg Ser Ala Ala Ser Arg Pro Thr
1               5                  10                  15

Glu Arg Pro Arg Ala Pro Ala Arg Ser Ala Ser Arg Pro Arg Arg Val
            20                  25                  30

Asp

<210> SEQ ID NO 6
<211> LENGTH: 18
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 6

Leu Leu Ile Ile Leu Arg Arg Arg Ile Arg Lys Gln Ala His Ala His
1               5                  10                  15

Ser Lys

<210> SEQ ID NO 7
<211> LENGTH: 16
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 7

Arg Val Ile Arg Val Trp Phe Gln Asn Lys Arg Cys Lys Asp Lys Lys
1               5                  10                  15
```

```
<210> SEQ ID NO 8
<211> LENGTH: 24
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 8

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 9
<211> LENGTH: 37
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 9

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 10
<211> LENGTH: 28
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 10

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 11
<211> LENGTH: 27
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 11

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 12
<211> LENGTH: 21
<212> TYPE: PRT
<213> ORGANISM: Artificial Sequence
<220> FEATURE:
<223> OTHER INFORMATION: PEPTIDE WILL BE CREATED USING CONVENTIONAL
      MEANS
```

<400> SEQUENCE: 12

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 13
<211> LENGTH: 11
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 13

Arg Arg Arg Arg Arg Arg Arg Arg Arg Arg Arg
1               5                   10

<210> SEQ ID NO 14
<211> LENGTH: 18
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 14

Lys Leu Ala Leu Lys Leu Ala Leu Lys Ala Leu Lys Ala Ala Leu Lys
1               5                   10                  15

Leu Ala

<210> SEQ ID NO 15
<211> LENGTH: 21
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 15

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 16
<211> LENGTH: 21
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 16

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 17
<211> LENGTH: 24
<212> TYPE: PRT
<213> ORGANISM: Artificial Sequence
<220> FEATURE:

```
<223> OTHER INFORMATION: PEPTIDE WILL BE CREATED USING CONVENTIONAL
      MEANS

<400> SEQUENCE: 17

Gly Ala Leu Phe Leu Gly Trp Leu Gly Ala Ala Gly Ser Thr Met Gly
1               5                  10                  15

Ala Pro Lys Lys Lys Arg Lys Val
            20

<210> SEQ ID NO 18
<211> LENGTH: 30
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 18

Trp Glu Ala Lys Leu Ala Lys Ala Leu Ala Lys Ala Leu Ala Lys His
1               5                  10                  15

Leu Ala Lys Ala Leu Ala Lys Ala Leu Lys Ala Cys Glu Ala
            20                  25                  30

<210> SEQ ID NO 19
<211> LENGTH: 20
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 19

Gly Leu Phe Lys Ala Leu Leu Lys Leu Leu Lys Ser Leu Trp Lys Leu
1               5                  10                  15

Leu Leu Lys Ala
            20

<210> SEQ ID NO 20
<211> LENGTH: 20
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 20

Gly Leu Phe Arg Ala Leu Leu Arg Leu Leu Arg Ser Leu Trp Arg Leu
1               5                  10                  15

Leu Leu Arg Ala
            20

<210> SEQ ID NO 21
<211> LENGTH: 9
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 21

Ala Gln Ser Gln Ala Gly Ser Leu Val
1               5

<210> SEQ ID NO 22
<211> LENGTH: 9
```

```
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 22

Gln Lys Tyr Val Gln Glu Glu Arg Leu
1               5

<210> SEQ ID NO 23
<211> LENGTH: 9
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 23

Gln Asn Arg Lys Glu Met Val Tyr Arg
1               5

<210> SEQ ID NO 24
<211> LENGTH: 9
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 24

Pro Ile Arg Glu Val Glu Asp Glu Cys
1               5

<210> SEQ ID NO 25
<211> LENGTH: 9
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 25

Ala Gln Ser Lys Asp Gly Ser Ile Val
1               5

<210> SEQ ID NO 26
<211> LENGTH: 10
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 26

Leu Pro Phe Glu Leu Arg Gly His Leu Val
1               5                   10

<210> SEQ ID NO 27
<211> LENGTH: 10
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 27

Gln Asp Ile Ile Asp Leu Gln Thr Glu Val
```

```
                1               5                    10

<210> SEQ ID NO 28
<211> LENGTH: 9
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 28

Tyr Lys Thr Asp Gly Ile Thr Val Val
1               5

<210> SEQ ID NO 29
<211> LENGTH: 9
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 29

Pro Ser Val Lys Ile Ala Thr Leu Val
1               5

<210> SEQ ID NO 30
<211> LENGTH: 9
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 30

Gly Gly Lys Lys Lys Glu Thr Leu Val
1               5

<210> SEQ ID NO 31
<211> LENGTH: 9
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 31

Pro Gly Phe Ala Ser Glu Ser Lys Val
1               5

<210> SEQ ID NO 32
<211> LENGTH: 9
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 32

Ser Arg Thr Arg Arg Glu Thr Gln Leu
1               5

<210> SEQ ID NO 33
<211> LENGTH: 9
<212> TYPE: PRT
<213> ORGANISM: Artificial Sequence
<220> FEATURE:
<223> OTHER INFORMATION: PEPTIDE WILL BE CREATED USING CONVENTIONAL
```

-continued

```
      MEANS

<400> SEQUENCE: 33

Asp Glu Asp Glu Gln Val Ser Ala Val
1               5

<210> SEQ ID NO 34
<211> LENGTH: 9
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 34

Met Ala Arg Thr Ala Arg Ser Lys Val
1               5

<210> SEQ ID NO 35
<211> LENGTH: 9
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 35

Gln Lys Val Arg Asn Val Thr Leu Val
1               5

<210> SEQ ID NO 36
<211> LENGTH: 22
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 36

Gly Arg Lys Lys Arg Arg Gln Arg Arg Arg Pro Pro Gln Ala Gln Ser
1               5                   10                  15

Gln Ala Gly Ser Leu Val
            20

<210> SEQ ID NO 37
<211> LENGTH: 22
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 37

Gly Arg Lys Lys Arg Arg Gln Arg Arg Arg Pro Pro Gln Ala Gln Ser
1               5                   10                  15

Lys Asp Gly Ser Ile Val
            20

<210> SEQ ID NO 38
<211> LENGTH: 22
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 38
```

```
Gly Arg Lys Lys Arg Arg Gln Arg Arg Pro Pro Gln Tyr Lys Thr
1               5                   10                  15

Asp Gly Ile Thr Val Val
            20
```

<210> SEQ ID NO 39
<211> LENGTH: 22
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 39

```
Gly Arg Lys Lys Arg Arg Gln Arg Arg Pro Pro Gln Gly Gly Lys
1               5                   10                  15

Lys Lys Glu Thr Leu Val
            20
```

<210> SEQ ID NO 40
<211> LENGTH: 22
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 40

```
Gly Arg Lys Lys Arg Arg Gln Arg Arg Pro Pro Gln Ser Arg Thr
1               5                   10                  15

Arg Arg Glu Thr Gln Leu
            20
```

<210> SEQ ID NO 41
<211> LENGTH: 9
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 41

```
Ala Gln Ser Lys Asp Gly Ala Ile Ala
1               5
```

<210> SEQ ID NO 42
<211> LENGTH: 9
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 42

```
Tyr Lys Thr Asp Gly Ile Ala Val Ala
1               5
```

<210> SEQ ID NO 43
<211> LENGTH: 22
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 43

```
Gly Arg Lys Lys Arg Arg Gln Arg Arg Pro Pro Gln Ala Gln Ser
1               5                   10                  15

Lys Asp Gly Ala Ile Ala
                20
```

<210> SEQ ID NO 44
<211> LENGTH: 22
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 44

```
Gly Arg Lys Lys Arg Arg Gln Arg Arg Pro Pro Gln Tyr Lys Thr
1               5                   10                  15

Asp Gly Ile Ala Val Ala
                20
```

<210> SEQ ID NO 45
<211> LENGTH: 68
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 45

```
Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
                20                  25                  30

Ala Leu Asp Gly Lys Met Glu Thr Gly Asp Val Ile Val Ser Val Asn
            35                  40                  45

Asp Thr Cys Val Leu Gly His Thr His Ala Gln Val Val Lys Ile Phe
        50                  55                  60

Gln Ser Ile Pro
65
```

<210> SEQ ID NO 46
<211> LENGTH: 76
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 46

```
Lys Glu Thr Gly Phe Gly Phe Arg Ile Leu Gly Gly Asn Glu Pro Gly
1               5                   10                  15

Glu Pro Ile Tyr Ile Gly His Ile Val Pro Leu Gly Ala Ala Asp Thr
                20                  25                  30

Asp Gly Arg Leu Arg Ser Gly Asp Glu Leu Ile Cys Val Asp Gly Thr
            35                  40                  45

Pro Val Ile Gly Lys Ser His Gln Leu Val Val Gln Leu Met Gln Gln
        50                  55                  60

Ala Ala Lys Gln Gly His Val Asn Leu Thr Val Arg
65                  70                  75
```

<210> SEQ ID NO 47
<211> LENGTH: 81

```
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 47

Gly Arg Lys Lys Arg Arg Gln Arg Arg Pro Pro Gln Arg Lys Ser
1               5                   10                  15

Ser Arg Gly Phe Gly Phe Thr Val Val Gly Gly Asp Glu Pro Asp Glu
            20                  25                  30

Phe Leu Gln Ile Lys Ser Leu Val Leu Asp Gly Pro Ala Ala Leu Asp
                35                  40                  45

Gly Lys Met Glu Thr Gly Asp Val Ile Val Ser Val Asn Asp Thr Cys
            50                  55                  60

Val Leu Gly His Thr His Ala Gln Val Val Lys Ile Phe Gln Ser Ile
65                  70                  75                  80

Pro

<210> SEQ ID NO 48
<211> LENGTH: 89
<212> TYPE: PRT
<213> ORGANISM: Artificial Sequence
<220> FEATURE:
<223> OTHER INFORMATION: PEPTIDE WILL BE CREATED USING CONVENTIONAL
      MEANS

<400> SEQUENCE: 48

Gly Arg Lys Lys Arg Arg Gln Arg Arg Pro Pro Gln Lys Glu Thr
1               5                   10                  15

Gly Phe Gly Phe Arg Ile Leu Gly Gly Asn Glu Pro Gly Glu Pro Ile
            20                  25                  30

Tyr Ile Gly His Ile Val Pro Leu Gly Ala Ala Asp Thr Asp Gly Arg
            35                  40                  45

Leu Arg Ser Gly Asp Glu Leu Ile Cys Val Asp Gly Thr Pro Val Ile
        50                  55                  60

Gly Lys Ser His Gln Leu Val Val Gln Leu Met Gln Gln Ala Ala Lys
65                  70                  75                  80

Gln Gly His Val Asn Leu Thr Val Arg
                85
```

PEPTIDE-BASED MOLECULES FOR MODULATING CAR EXPRESSION OR ACCESSIBILITY AND USES THEREOF

RELATED APPLICATIONS

This application is claiming the benefit, under 35 U.S.C. § 119(e), of the provisional application filed on Jul. 9, 2015, under 35 U.S.C. § 111(b), which was granted Ser. No. 62/190,461. Application Ser. No. 62/190,461 is hereby incorporated by reference in its entirety to the extent permitted by law.

STATEMENT REGARDING FEDERALLY SPONSORED RESEARCH OR DEVELOPMENT

This invention was made with government support under A1090625 awarded by the National Institutes for Health. The government has certain rights in the invention.

FIELD OF THE INVENTION

The present invention relates to modulation of the expression or accessibility of viral receptors. In particular, the invention relates to modulation of the expression or accessibility of coxsackievirus and adenovirus receptors (CAR). The invention more specifically relates to using peptide-based molecules to modulate the expression or accessibility of the receptors. In specific embodiments, the peptide-based molecules are cell-permeable. The cell-permeable peptide-based molecules may include PDZ-binding or PDZ-decoy domains. The invention also relates to use of modulation of the expression or accessibility of viral receptor to treat viral disease, lessen infection from a viral disease, or enhance efficacy of gene therapy systems.

BACKGROUND OF THE INVENTION

The performance of viral-mediated gene therapy could be enhanced if there were treatments that had the ability to modulate expression or accessibility of the viral receptors on the cell surface. Such increased expression or accessibility of viral receptors could increase the efficacy of a virus-based therapeutic molecule which, in turn, would allow for a lower burden of gene therapy vector administered to the individual undergoing treatment.

In particular, modulation of the expression or accessibility of coxsackievirus and adenovirus receptors (CAR) is an especially desirable target because most gene therapy technologies rely on adenovirus based systems or any of the Coxsackievirus-based systems being developed. The success of a gene therapy system relies both on the copy number of modified viruses delivered to a single host cell and the number of host cells infected with the modified virus. More copies of the modified viral genomes entering into a host cell allows for higher levels of beneficial gene expression and higher therapeutic protein production to treat the target disease. Similarly, if more host cells take up the therapeutic gene, than the greater treatment/correction of target diseases. Therefore, increasing the amount of viral receptor available on a host cell will increase the number of genetically modified virus that enter a host cell and/or will increase the number of host cells that take up the beneficial virus.

In addition, Coxsackie B viruses, adenoviruses, and Swine Vesicular Disease Virus are serious disease-causing viruses. Currently, no specific therapy exists to treat or lessen the chance of infection from Coxsackie B viruses, adenoviruses, and Swine Vesicular Disease Virus. Supportive care remains the standard treatment. With an ability to modulate the expression or accessibility of CAR, new treatments could be made readily available that protect the host by reducing the amount of viral receptor available on the cell surface thereby (1) decreasing the chance that a virus will enter into a host cell, (2) decreasing the amount of virus entering into a host cell to slow the ability of the virus to take over the cell, (3) allowing the immune system of the host more time to react if a smaller number of viruses do enter the host cell, (4) decreasing viral-induced disease by slowing the time course of infection, (5) blocking or limiting spread of the virus to other cells or organs if an individual is affected or (6) limiting the spread of progeny virus to other individuals in the community by decreasing the number of infectious virions produced.

The current invention shows that certain peptide-based molecules can modulate expression or accessibility of CAR, allowing for better success with gene therapy or treatment of Coxsackie B viruses, adenoviruses, or Swine Vesicular Disease Virus.

SUMMARY OF THE INVENTION

Peptides comprising a cell-permeating peptide (CPP) domain and at least one of a PDZ binding domain or PDZ decoy domain are disclosed. In particular embodiments, a peptide with a first peptide portion having substantial homology with a first peptide sequence selected from the group: SEQ ID NOs: 1-20 and (ii) a second peptide portion having substantial homology with a second peptide sequence selected from the group: SEQ ID NOs: 21-35, 45, and 46, is disclosed.

A method of increasing or decreasing apical surface localization of CAR in a target cell is provided herein. Methods for reducing CAR-mediated viral infection, protecting a target cell from CAR mediated viral infection, and increasing efficacy of adenovirus based gene therapy using the peptides are also disclosed.

BRIEF DESCRIPTION OF THE DRAWINGS

The above, as well as other advantages of the present invention, will become readily apparent to those skilled in the art from the following detailed description when considered in the light of the accompanying drawings in which.

SEQUENCE LISTING

Figure 1:
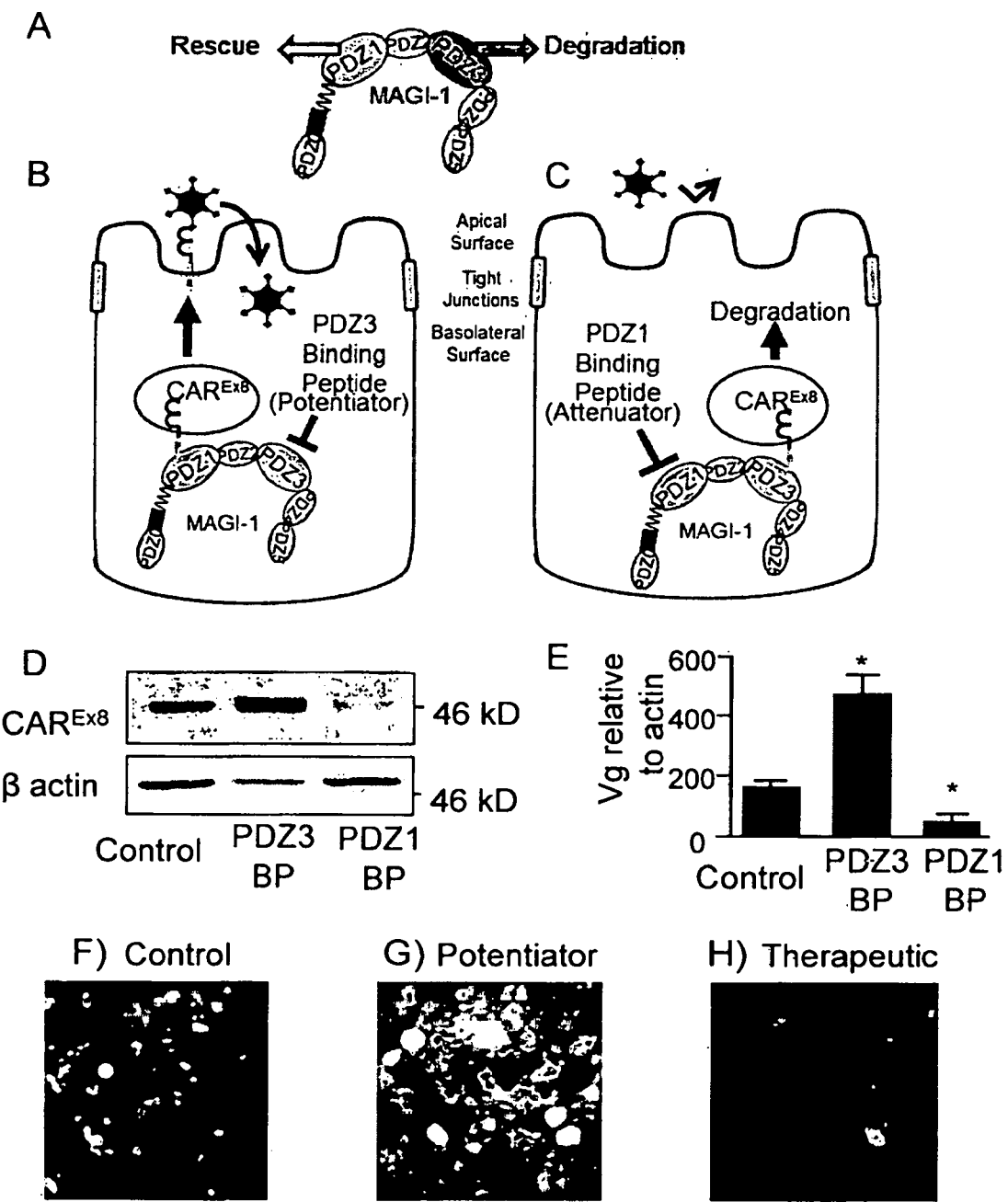
FIG. 1 shows that MAGI-1 PDZ binding peptides (BP) can alter $CAR^{Ex8}$ apical protein levels and AdV infection.

The nucleic and amino acid sequences listed in the accompanying sequence listing are shown using standard letter abbreviations for nucleotide bases, and three letter code of amino acids, as defined in 37 C.F.R. § 1.822.

Only one strand of each nucleic acid sequence may be shown, but the complementary strand is understood as included by any reference to the displayed strand. In the accompanying sequence listing:

SEQ ID NO: 1 shows the amino acid sequence of TAT.
SEQ ID NO: 2 shows the amino acid sequence of AP.
SEQ ID NO: 3 shows the amino acid sequence of poly arginine.
SED ID NO: 4 shows the amino acid sequence of Sim2.
SED ID NO: 5 shows the amino acid sequence of VP22
SED ID NO: 6 shows the amino acid sequence of pVEC
SED ID NO: 7 shows the amino acid sequence of pISL
SED ID NO: 8 shows the amino acid sequence of hCT
SED ID NO: 9 shows the amino acid sequence of LL-37
SED ID NO: 10 shows the amino acid sequence of Mouse PrP (1-28)
SED ID NO: 11 shows the amino acid sequence of Transportan (TP)
SED ID NO: 12 shows the amino acid sequence of TP10
SED ID NO: 13 shows the amino acid sequence of Arg 1
SED ID NO: 14 shows the amino acid sequence of MAP
SED ID NO: 15 shows the amino acid sequence of Pep-1
SED ID NO: 16 shows the amino acid sequence of Pep-2
SED ID NO: 17 shows the amino acid sequence of MPG
SED ID NO: 18 shows the amino acid sequence of KALA
SED ID NO: 19 shows the amino acid sequence of ppTG1
SED ID NO: 20 shows the amino acid sequence of ppTG20
SEQ ID NO: 21 shows the amino acid sequence of ESAM.
SEQ ID NO: 22 shows the amino acid sequence of Slo1a.
SEQ ID NO: 23 shows the amino acid sequence of Slo1b.
SEQ ID NO: 24 shows the amino acid sequence of Slo1c.
SEQ ID NO: 25 shows the amino acid sequence of CAR$^{EX7}$.
SEQ ID NO: 26 shows the amino acid sequence of Nephrin.
SEQ ID NO: 27 shows the amino acid sequence of BAI-1.
SEQ ID NO: 28 shows the amino acid sequence of CAR$^{EX8}$.
SEQ ID NO: 29 shows the amino acid sequence of Ad9 E4Orf1.
SEQ ID NO: 30 shows the amino acid sequence of NET1.
SEQ ID NO: 31 shows the amino acid sequence of Beta1AR.
SEQ ID NO: 32 shows the amino acid sequence of HPV E6.
SEQ ID NO: 33 shows the amino acid sequence of RapGEP.
SEQ ID NO: 34 shows the amino acid sequence of Influenza A virus NS1.
SEQ ID NO: 35 shows the amino acid sequence of JAM4.
SEQ ID NO: 36 shows the amino acid sequence of TAT-ESAM.
SEQ ID NO: 37 shows the amino acid sequence of TAT-CAR$^{EX7}$.
SEQ ID NO: 38 shows the amino acid sequence of TAT-CAR$^{EX8}$.
SEQ ID NO: 39 shows the amino acid sequence of TAT-NET1.
SEQ ID NO: 40 shows the amino acid sequence of TAT-HPV E6.
SEQ ID NO: 41 shows the amino acid sequence of control peptide CAR$^{EX7}$-AA.
SEQ ID NO: 42 shows the amino acid sequence of control peptide CAR$^{EX8}$-AA.
SEQ ID NO: 43 shows the amino acid sequence of control peptide TAT-CAR$^{EX7}$-AA.
SEQ ID NO: 44 shows the amino acid sequence of control peptide TAT-CAR$^{EX8}$-AA.
SEQ ID NO: 45 shows the amino acid sequence of MAGI-1-PDZ1.
SEQ ID NO: 46 shows the amino acid sequence of MAGI-1-PDZ3.
SEQ ID NO: 47 shows the amino acid sequence of TAT-MAGI-1-PDZ1.
SEQ ID NO: 48 shows the amino acid sequence of TAT-MAGI-1-PDZ3.

The "Sequence Listing" material in the 16,105 byte ASCII text file named 1-25003-seq1.txt, created on Jul. 16, 2018, is hereby incorporated-by-reference in its entirety.

DETAILED DESCRIPTION

A. In General

The embodiments herein described are not intended to be exhaustive or to limit the invention to the precise forms disclosed. They are chosen and described to explain the principles of the invention and the application of the method to practical uses so that others skilled in the art may practice the invention.

As used in the specification and the appended claims, the singular forms "a," "an" and "the" include plural referents unless the context clearly dictates otherwise. Thus, for example, "a cell" may refer to a population of cells or reference to "a cell-permeable peptides" may include both reference to a single cell-permeable peptide and reference to a plurality of cell-permeable peptides. Likewise, the use of a plural noun is to be construed as including the singular thereof, unless the context clearly dictates otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Ranges can be expressed herein as from "about" one particular value, and/or to "about" another particular value. When values are expressed as approximations, by use of the antecedent "about", it will be understood that the particular value forms another embodiment.

The use of the word "or" in this description is used conjunctively to mean one of the series, or any combination thereof, unless the context clearly dictates otherwise.

All publications and documents cited herein are incorporated to the extent permitted by law. In case of any conflict, this disclosure prevails. The citation of any document is not to be construed as an admission that it is prior art with respect to the present disclosure.

B. Terms and Abbreviations

Unless otherwise noted, technical terms are used according to conventional usage. Definitions of common terms in molecular biology may be found in Benjamin Lewin, Genes V., published by Oxford University Press, 1994 (ISBN 0-19-854287-9); Kendre et al. (eds.), *The Encyclopedia of Molecular Biology*, published by Blackwell Science Ltd., 1994 (ISBN 0-632-2182-9); and Robert A. Meyers (ed.), Molecular Biology and Biotechnology: a Comprehensive Desk Reference, published by VCH Publishers, Inc. 1995 (ISBN 1-56081-569-8).

Terms

"Transmembrane protein" refers to a protein that has a portion of its protein sequence projecting outside of a cell (i.e. the extracellular domain), a portion of a protein running through the lipid membrane (i.e. the transmembrane domain), and/or a portion of a protein projecting into the cytoplasm inside of a cell (i.e. the cytoplasmic domain).

"Polarized cell" refers to a differentiated cell that has distinct regions which are capable of functioning in distinct ways. For example, epithelial cells have a portion thereof external to the body and exposed to the external world, e.g., the surface of skin (i.e. the apical surface) and a portion internal to the body (i.e. the basolateral surface). The lung airway epithelium is composed of polarized cells. For example, breathing allows air to enter the lung and is in contact with the apical surface. However, interstitial fluid (e.g. blood) is in contact with the basolateral surface. Neurons also have polarity with an axon leading to the cell body and neurites leading to connections with the axons of other neurons creating a polarized network of excitatory cells.

"CAR" and "Coxsackievirus and Adenovirus Receptor" refer to a cell-cell adhesion protein and viral receptor. There are two transmembrane isoforms of CAR, i.e., $CAR^{EX7}$ and $CAR^{EX8}$. Such isoforms differ in the extreme C-termini and although both function as viral receptors, their normal functions differ as cellular adhesion proteins.

"$CAR^{EX7}$" refers to a basolateral adhesion protein able to traffic PDZ-domain-containing proteins to cell-cell junctions. In polarized cells, the extracellular domain of $CAR^{EX7}$ is not exposed to the outside world but rather the basolateral interstitial fluid between cells. $CAR^{EX7}$ is responsible for holding two adjacent cells together and causing PDZ-domain containing proteins to localize at basolateral cell-cell junctions. $CAR^{EX7}$ functions to traffic, drive, or guide MAGI-1 to cell junctions.

"$CAR^{EX8}$" refers to an apical adhesion protein. In polarized epithelial cells, the extracellular domain of $CAR^{EX8}$ is exposed to the external world or air exposed apical surface where it can come into contact with viruses transmitted via air (such as, e.g., via droplets like those produced by a sneeze). $CAR^{EX8}$ is an adhesion protein for white blood cells, such as, e.g., neutrophils or macrophages or T cells, which transmigrate from inside the body to outside the body (i.e., to the apical surface) to kill and/or eliminate microbes and/or other molecules (such as, e.g., pollen, dirt, etc.) which enter the airway and/or other epithelial surfaces. $CAR^{EX8}$ is regulated by MAGI-1. For example, if $CAR^{Ex8}$ binds to and/or interacts with the PDZ3 domain of MAGI-1, $CAR^{Ex8}$ will be degraded or modified or retained within the cell and unable to reach the apical surface. Alternatively, if $CAR^{EX8}$ binds to or interacts with the PDZ1 domain of MAGI-1, $CAR^{EX8}$ is not degraded and can reach the apical surface of polarized cells "PDZ domain," a term derived from the names of the first three proteins identified to contain the domain: Post-Synaptic Density-95/*Drosophila* Disc Large Tumor Suppressor/ Zonula Occludens 1 protein (i.e. PSD-95/DIg1/ZO-1), refers to an approximately 90 amino acid protein-based sequences that can fold into an independent region of the overall protein. Such protein-based sequences may mediate protein-protein interactions by binding to a PDZ-binding domain. Only a subset of proteins within a cell may contain PDZ domains.

"PDZ-binding domain" refers to a 4 amino acid motif often found at a terminus of proteins that can interact with PDZ domains. Only a subset of proteins within a cell may contain PDZ-binding domains.

"PDZ1-binding peptide" may refer to any peptide comprising both (i) a first peptide portion having substantial homology with a first peptide sequence selected from the group: SEQ ID NOs: 1-20 and (ii) a second peptide portion having substantial homology with a second peptide sequence selected from the group: SEQ ID NOs: 28-35. The two peptide portions that make up the PDZ1-binding peptide may have sequence separating them or may be continuous. The two peptide portions may be presented in any order. In certain embodiments, the first peptide portion having substantial homology with a first peptide sequence selected from the group: SEQ ID NOs: 1-20 will be closer to the 5' end than the second peptide portion having substantial homology with a second peptide sequence selected from the group: SEQ ID NOs: 28-35. In certain embodiments, the PDZ1-binding peptide will have substantial homology with a peptide sequence selected from the group: SEQ ID NO: 39 and 40.

"PDZ3-binding peptide" may refer to any peptide comprising both (i) a first peptide portion having substantial homology with a first peptide sequence selected from the group: SEQ ID NOs: 1-20 and (ii) a second peptide portion having substantial homology with a second peptide sequence selected from the group: SEQ ID NOs: 21-29. The two peptide portions that make up the PDZ3-binding peptide may have sequence separating them or may be continuous. The two peptide portions may be presented in any order. In certain embodiments, the first peptide portion having substantial homology with the first peptide sequence selected from the group: SEQ ID NOs: 1-20 will be closer to the 5' end than the second peptide portion having substantial homology with the second peptide sequence selected from the group: SEQ ID NOs: 21-29. In certain embodiments, the PDZ3-binding peptide will have substantial homology with a peptide sequence selected from the group: SEQ ID NO: 36, 37, and 38.

"PDZ1-decoy" may refer to any peptide comprising both (i) a first peptide portion having substantial homology with a first peptide sequence selected from the group: SEQ ID NOs: 1-20 and (ii) a peptide portion having substantial homology with SEQ ID NO: 45. The two peptide portions that make up the PDZ1-decoy may have sequence separating them or may be continuous. The two peptide portions may be presented in any order. In certain embodiments, the first peptide portion having substantial homology with the first peptide sequence selected from the group: SEQ ID NOs: 1-20 will be closer to the 5' end than the second peptide portion having substantial homology with SEQ ID NO: 45. In certain embodiments, the PDZ1-decoy will have substantial homology with SEQ ID NO: 47.

"PDZ3-decoy" may refer to any peptide comprising both (i) a first peptide portion having substantial homology with a first peptide sequence selected from the group: SEQ ID NOs: 1-20 and (ii) a second peptide portion having substantial homology with SEQ ID NO: 46. The two peptide portions that make up the PDZ3-decoy may have sequence separating them or may be continuous. The two peptide portions may be presented in any order. In certain embodiments, the first peptide portion having substantial homology with the first peptide sequence selected from the group of: SEQ ID NOs: 1-20 will be closer to the 5' end than the second peptide portion having substantial homology with SEQ ID NO: 46. In certain embodiments, the PDZ3-decoy will have substantial homology with SEQ ID NO: 48.

"MAGI-1" refers to a membrane-associated guanylate kinase with an inverted domain structure-1, also known as Membrane Associated Guanylate Kinase, WW and PDZ Domain Containing 1, BAI1-Associated Protein 1, and Atrophin-1-Interacting Protein 3. MAGI-1 is a large protein with several types of protein-protein interaction domains including, e.g., up to six PDZ domains, two WW domains, and a guanylate kinase domain, that altogether can act as a scaffold in the cell to bring several interacting proteins together and create a signaling center, wherein each domain can interact with a different protein that has a unique function and can affect the other proteins being held in close proximity by binding other MAGI-1 domains, theoretically including up to at least nine simultaneous interactions. MAGI-1 is alternatively spliced such that it may include all domains and/or only some domains. PDZ1 (SEQ ID NO: 45) and PDZ3 (SEQ ID NO: 46) are of particular relevance to this disclosure.

"Substantially homologous" or "substantial homology" means a degree of sequence homology to any one of the peptides having the amino acid sequences set forth in SEQ ID NOs: 1-48 where the degree of sequence homology is preferably at least 70%, most preferably at least 80%, and even more preferably at least 90% or even 95%. It also means that one or more particular amino acid in any given peptide may be modified as is known in the art without exceeding the scope of the invention. For example, one or more amino acids may be replaced with artificial amino acids or the peptide could be conjugated to a marker molecule or dye.

Abbreviations

CAR: Coxsackievirus and adenovirus receptor; qPCR: quantitative polymerase chain reaction; MDCK: Madin-Darby canine kidney epithelial cells; AdV5-B-Gal: adenovirus beta galactose delivery vector; Vg: viral genome; MG 132: a proteasome inhibitor; CHX: cyclohexamide; DAPI: a nucleic acid stain; kDa: kilodalton; AdV5-Cre; adenovirus cre recombinase delivery vector; tdT: tdTomato transmembrane red fluorescent protein (used in the context of transgenic tdTomato-LoxP-GFP genetically altered mice); GFP: green fluorescent protein; RT-PCR: reverse transcriptase polymerase chain reaction; HIV-TAT-CPP: HIV derived "transactivator of transcription" cell penetrating peptide; TAMRA: 5-Carboxytetramethylrhodamine red fluorescent dye; CHO: Chinese hamster ovary cells; ER: endoplasmic reticulum; TER: transepithelial resistance; Dox: doxycycline; FLAG: protein tag; PBS; phosphate buffered saline; AAV: adeno-associated virus; RIP: regulated intramembrane proteolysis; AdV: adenovirus, CPP: cell penetrating (permeable) peptide (see Table 2 for a non-exhaustive list of possible CPPs that can be used in accordance with the invention).

C. Description of Various Embodiments

As described above, the primary receptor for Coxsackie B viruses, adenoviruses, and Swine Vesicular Disease Virus is the Coxsackie and adenovirus receptor (CAR). The abundance of CAR on a host cell surface is a major predictor of the susceptibility of host cells to adenoviruses, whether wild-type or as used as a gene therapy vector. Two opposing interactions within a single host cell scaffolding protein, membrane-associated guanylate kinase with inverted domain structure-1 (hereinafter MAGI-1), has provided the means to directly affect the amount of CAR accessible for viral infection both in vitro and in vivo.

Firstly, disclosed is an approach to block the interaction between $CAR^{EX8}$ and MAGI-1 by administering small, peptide-based molecules, which are less than 50 amino acids in length, that are cell permeable and that interact with the first (i.e., PDZ1) and/or third (i.e., PDZ3) PDZ domains of MAGI-1. In embodiments, disruption of the $CAR^{EX8}$-PDZ1 interaction attenuates $CAR^{EX8}$ intracellular and cell surface protein levels. In embodiments, disruption of the PDZ3 interaction potentiates $CAR^{EX8}$ intracellular and cell surface protein levels. As shown in Table 1, a list of suitable, but not limiting, potential peptide-based potentiator and attenuator molecules are disclosed.

Secondly, disclosed is an approach utilizing peptide-based molecules having decoy cell permeable MAGI-1 PDZ1 or PDZ3 domains. In embodiments, the individual decoy PDZ1 domain is able to bind $CAR^{EX8}$, to sequester $CAR^{EX8}$ from interacting with full length endogenous MAGI-1, and to potentiate $CAR^{EX8}$ intracellular and cell surface protein levels. In contrast, in embodiments, the individual decoy PDZ3 domain is able to bind $CAR^{EX8}$, to sequester it from interacting with full length endogenous MAGI-1, and to hold $CAR^{EX8}$ within the cell or cause $CAR^{EX8}$ degradation. Thus, in embodiments, the individual PDZ3 domain attenuates $CAR^{EX8}$ intracellular and cell surface protein levels.

1. Attenuators and Methods of Using the Same

Small molecules that decrease CAR would be used as protection from or reduction of adenovirus (groups A, C-G), CAR binding adenoviruses from other species, group B Coxsackievirus infections, and Swine Vesicular Disease Virus. These small molecules could be applied proactively to protect susceptible populations or those entering a situation knowing they may be at risk of exposure (e.g. during an outbreak, during military training, healthcare providers, etc.), or could be applied after an infection has occurred to reduce the spread (e.g. within an individual or to others in the community) and burden of the disease.

2. Potentiators and Methods of Using the Same

Small molecules that increase CAR would be used to potentiate or to increase recombinant adenovirus (groups A, C-G), CAR-binding adenoviruses from other species, such as, but not limited to, canine or gorilla, and group B Coxsackievirus infections. These small molecules could be applied proactively to enhance adenovirus and group B Coxsackievirus as gene therapy vectors or oncolytic viral therapy for genetic and acquired diseases such as, but not limited in any way to, cystic fibrosis, asthma, chronic obstructive pulmonary disease (COPD), and cancers such as glioblastoma or lung cancer. These small molecules could be applied proactively as adjuvants to enhance adenovirus and group B Coxsackievirus immunization strategies for cancer and infectious diseases such as, but not limited to, metastatic melanoma or ebolavirus. Increasing the availability of CAR with these molecules is expected to decrease viral inoculum dose and increase specificity of target tissue uptake.

With regard to Table 1, PDZ-binding peptides described interact with MAGI-1 PDZ1 or PDZ3. In bold are the peptide sequences that are used in the examples that follow. Mutant control peptides may be created by replacing the last amino acid and −3 amino acids with alanine (i.e. . . . AXA).

With regard to Table 1, it is noted that the TAT cell permeable portion of the peptide-based molecules is provided to facilitate entry of the bioactive PDZ domain or binding domain into target cells, such as, e.g., host cells. It is further noted that such cell permeable portion of the peptide based molecules could be any number of available cell permeable peptides and/or polypeptides sequences known to those of ordinary skill in the art, which include, but are not limited to, TAT, antennapedia protein, or Sim2, or SEQ ID NO: 1-20.

In embodiments, the peptide-based molecules described herein are synthesized by standard commercially available procedures known to those of ordinary skill in the art. For example, such peptide-based molecules may be produced by standard methods known to those of ordinary skill in the art in peptide synthesizers, bacteria and/or eukaryotic cells such as, e.g., CHO cells. Moreover, PDZ domains may be produced according to methods known to those of ordinary skill in the art, such as, e.g., in bacteria and/or eukaryotic cells such as, e.g., CHO cells.

In embodiments, the peptide-based molecules described herein may be administered to and/or contacted with a target cell or tissue, such as, e.g., a host cell or lungs. For example, to administer and/or contact such peptide-based molecules with a target cell or tissue, the peptide-based molecules may be diluted in isotonic solutions such as, e.g., standard saline, phosphate-buffered saline, or the like. The peptide-based molecules may then be administered systemically and/or topically. More specifically, the peptide-based molecules may be administered via inhalation, aerosolization, nebulization, injection and/or other standard methods such as, e.g., topical creams.

It is expected that a single administration will have sufficient biological effect but readministration may be necessary depending on the application method or the desired result. For example, if there is an outbreak of wild-type adenovirus or Coxsackievirus, or other virus, multiple administrations may be required for full protection from viral infection. In contrast, to improve adenovirus and/or other virus-mediated gene therapy, a single administration may be sufficient for clinical efficacy.

Additionally in further embodiments, the administering and/or contacting is effective to control, treat, prevent, and/or correct an adenovirus infection and/or a Coxsackie virus infection. As shown in Table 3 below, adenovirus pathogenesis is associated with various diseases. In embodiments, the methods described herein could be effective to treat and/or prevent at least some of such diseases.

Small molecules that decrease CAR expression or accessibility would be used as protection from or reduction of adenovirus (groups A, C-G, see Table 3), CAR-binding adenoviruses from other species, group B Coxsackievirus infections, or Swine Vesicular Disease Virus. These small molecules could be applied proactively to protect susceptible populations or those entering a situation knowing they may be at risk of exposure (e.g. during an outbreak, during military training, healthcare providers, etc.), or could be applied after an infection has occurred to reduce the spread (e.g. within an individual or to others in the community) and burden of the disease.

In embodiments, while both of $CAR^{EX8}$ and $CAR^{Ex7}$ can bind to and/or interact with PDZ3 of MAGI-1, if $CAR^{EX8}$ does so, it will be degraded and/or modified and/or retained in the cell. However, if $CAR^{Ex7}$ binds to and/or interacts with PDZ3 of MAGI-1, it may traffic, drive, and/or guide MAGI-1 to basolateral junctions. Without being bound by the theory, it is believed that such mechanism may: (1) maintain low levels of $CAR^{EX8}$ in order to limit apical viral infection and inflammation by binding viruses or pro-inflammatory white blood cells, respectively; and/or (2) prevent MAGI-1 (and anything bound to and/or complexed therewith) from being trafficked to the apical surface.

Further, several approaches to controlling, modulating, treating, and/or preventing viral infection and inflammation associated with and/or correlated to the level of $CAR^{Ex8}$ at the apical surface of the epithelium have also been devised. In embodiments, peptide- and/or polypeptide-based molecules that are capable of modulating CAR expression on target cells are disclosed. More specifically, in embodiments, peptide- and/or polypeptide-based molecules that are capable of increasing and/or decreasing the level of CAR on cells, such as, e.g., host cells, are disclosed. Such peptide- and/or polypeptide-based molecules have been developed using two approaches to modulating the level of CAR, such as, e.g., the level of apical adenovirus receptor $CAR^{EX8}$.

D. Examples

The following non-limiting examples illustrate the methods and compositions of a selection of embodiments.

MAGI-1 PDZ binding peptides (BP) can alter $CAR^{EX8}$ apical protein levels and AdV infection. As shown in FIG. 1, MAGI-1 PDZ binding peptides (BP) can alter $CAR^{Ex8}$ apical protein levels and AdV infection. A) MAGI-1 PDZ1 can rescue $CAR^{Ex8}$ expression while PDZ3 decreases $CAR^{EX8}$ expression. B) Peptides that bind to PDZ3 will prevent degradation of $CAR^{Ex8}$ and rescue $CAR^{EX8}$ expression and C) peptides that bind to PDZ1 will prevent rescue of $CAR^{Ex8}$ and decrease $CAR^{Ex8}$ degradation. D) Apical surface-specific biotinylation of polarized MDCK epithelia treated with PDZ1 binding peptide decreases apical levels of $CAR^{EX8}$ while PDZ3 binding peptide increase apical $CAR^{EX8}$, relative to control. E) Treatment with PDZ3 binding peptide increases while PDZ1 binding peptide decreases AdV5-β-Gal entry as determined by qPCR for viral genomes (Vg). F) AdV5-Cre infection turns cells from red (uninfected) to green (infected) in tDT-mouse airway epithelial cells. Baseline infection in control-peptide treated airway epithelia show an even distribution of uninfected red cells and infected green cells. G) Upregulation of CAR with potentiator-peptide (PDZ3 binding peptide) significantly increases AdV5-Cre infection (mostly green cells). H) Downregulation of CAR with therapeutic peptide (PDZ1 binding peptide) significantly decreases AdV5-Cre infection (mostly red cells). *p<0.05.

Figure 2:
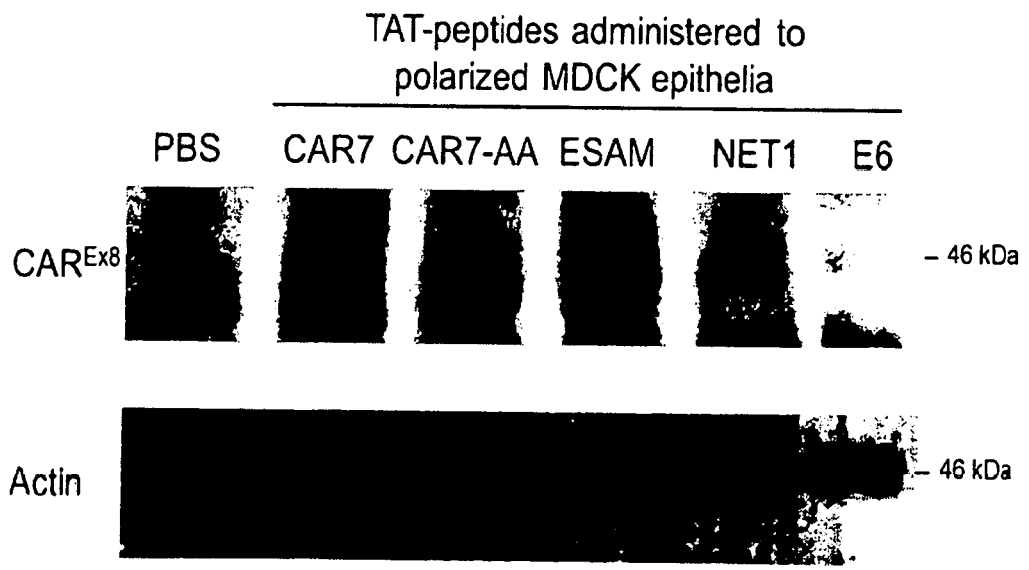
FIG. 2 is a blot of $CAR^{Ex8}$ and Actin expression in polarized MDCK epithelial cells treated with PBS (control), TAT-CAR7, TAT-CAR7-AA (control), TAT-ESAM, TAT-NET1, and TAT-E6 (see also Table 1)

FIG. 2 is blot of $CAR^{Ex8}$ and Actin expression in polarized MDCK epithelial cells treated with PBS (Control), TAT-CAR7, TAT-CAR7-AA (Control), TAT-ESAM, TAT-NET1, and TAT-E6. See Table 1.

Figure 3:
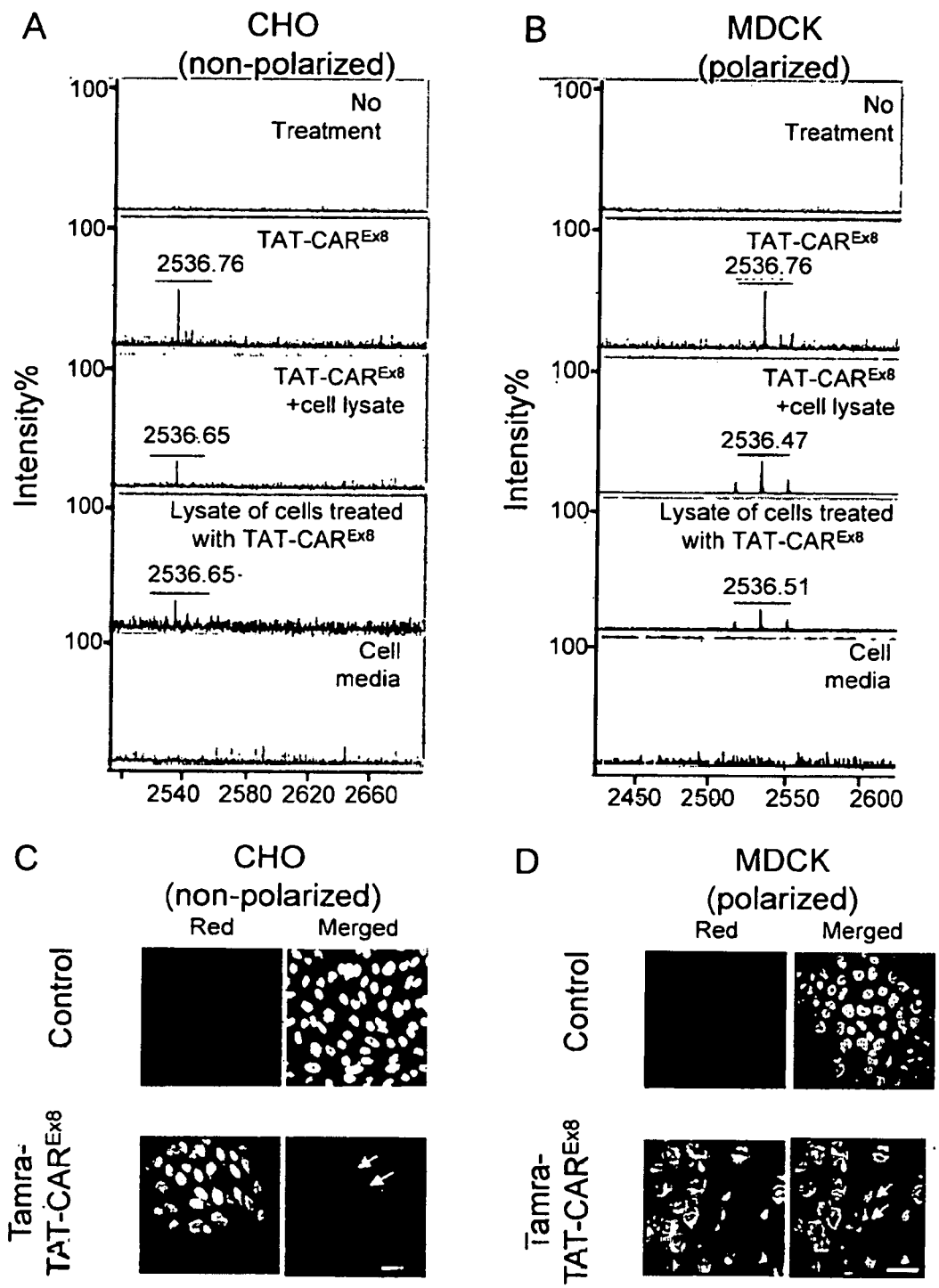
FIG. 3 shows that TAT-cell permeable peptides enter non-epithelial and epithelial cells.

FIG. 3. shows that TAT-cell permeable peptides enter non-epithelial and epithelial cells. MALDI-TOF analysis of $TAT-CAR^{Ex8}$ peptides associate with (A) CHO cells (non-epithelial) and (B) MDCK epithelia. A peak at m/z 2536 showed in both cell lines corresponded to the m/z of $TAT-CAR^{E}B$. CHO or MDCK were incubated with either $TAT-CAR^{Ex8}$ or vehicle for 1 hr at 37° C. Cell pellets obtained were used for MALDI-TOF. $TAT-CAR^{Ex8}$ enters cells and peaked at m/z 2536. (C) CHO or (D) MDCK cells were treated with either vehicle control (PBS) or fluorescently labelled $TAMRA-TAT-CAR^{Ex8}$. Peptide was detectable within 1 h after incubation inside cells. White arrows indicate ER/Golgi region of cell with intense TAMRA (red) fluorescence. 60× oil immersion confocal microscopy, White line=10 μm.

Figure 4:
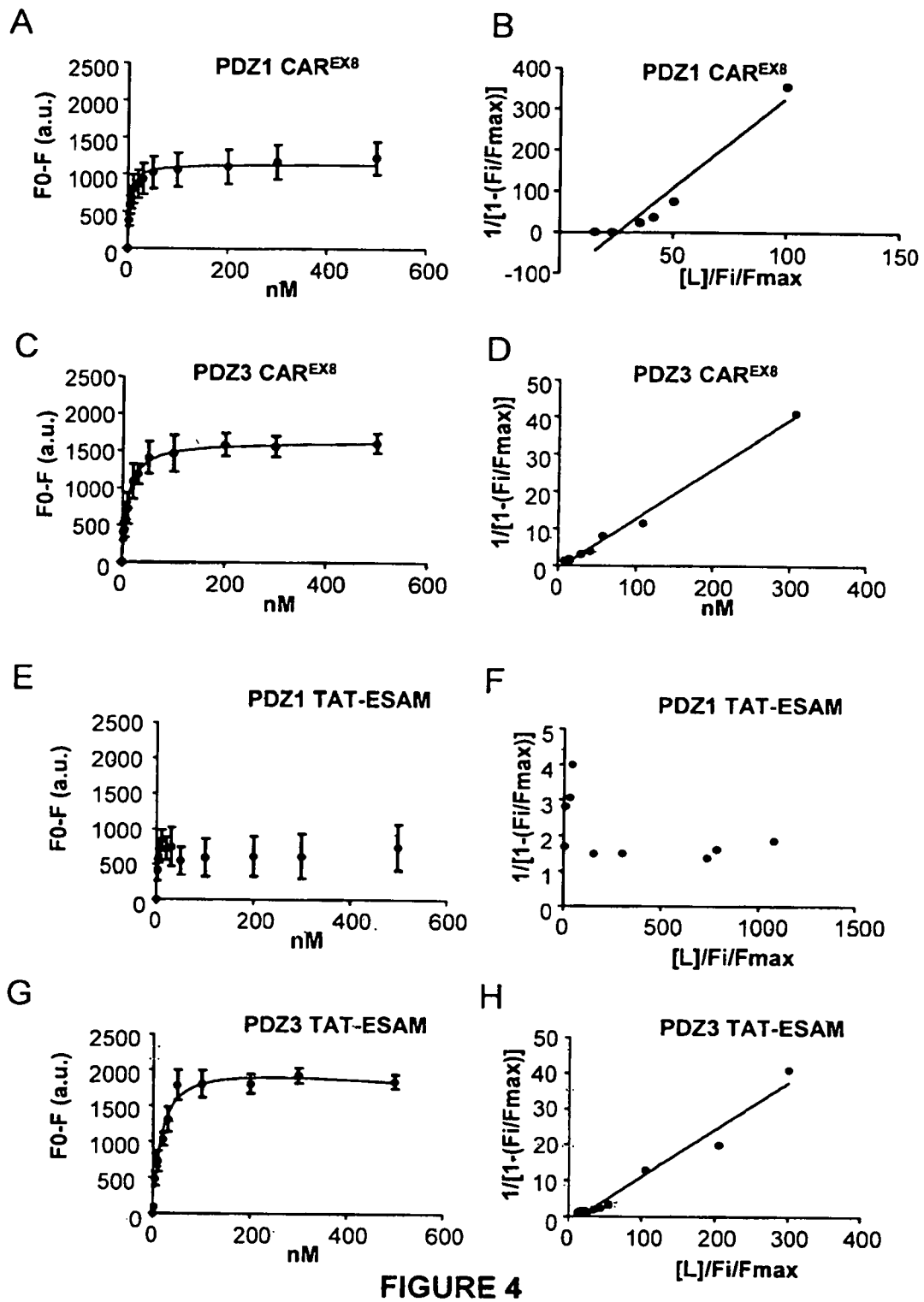
FIG. 4 shows that TAT-$CAR^{Ex8}$ binds to both MAGI-1 PDZ1 and PDZ3 domains and TAT-ESAM binds to MAGI-1 PDZ3 but not PZ1 domain.

FIG. 4 shows that $TAT-CAR^{Ex8}$ binds to both MAGI-1 PDZ1 and PDZ3 domains. Ligand binding assay between $TAT-CAR^{Ex8}$ and the purified MAGI-1 PDZ1 or PDZ3. Lack of binding to MAGI-1 PDZ2 domain was used as a control (not shown). $TAT-CAR^{Ex8}$ peptides bind to MAGI-1 PDZ1 (A, B; Kd=23±9 nM), and binds PDZ3 with higher affinity (C, D; Kd=4±2 nM). B, D) Double reciprocal plots are linear indicating a single binding site between the ligand and PDZ3 (D) and PDZ1 domain (B). (E) TAT-ESAM, a PDZ3 binding peptide, binds selectively to the MAGI-1 PDZ3 domain. Ligand binding assay between TAT-ESAM and purified MAGI-1 PDZ1 or PDZ-3. TAT-ESAM peptide does not bind to MAGI-1 PDZ1 (E, F) but does binds PDZ3 (G, H; Kd=17±5 nM). Double reciprocal plot shows (F) no curve indicating no binding to PDZ1 or (H) is linear indicating a single binding site between the ligand and PDZ3.

Figure 5:
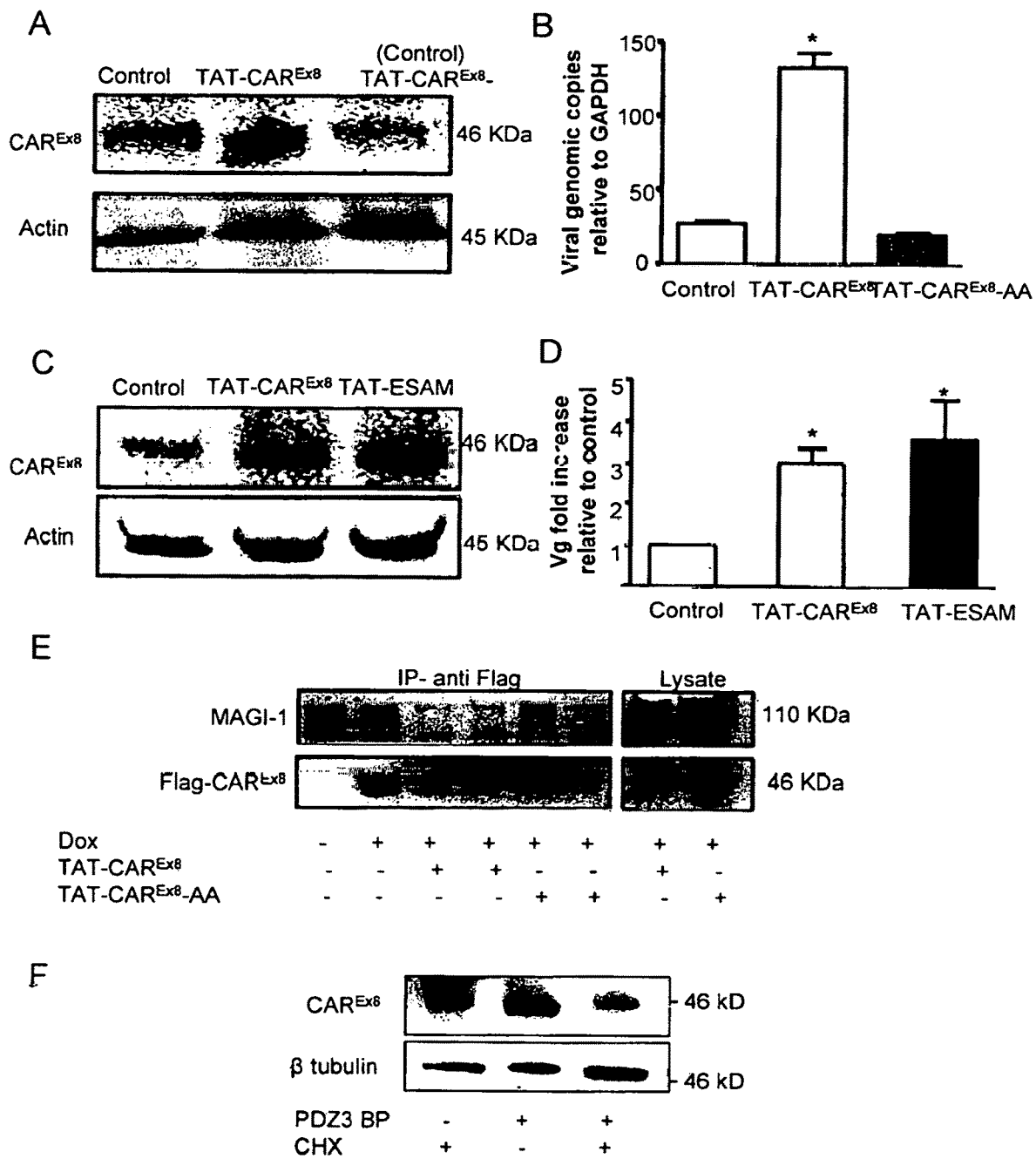
FIG. 5 shows that TAT-$CAR^{Ex8}$ and TAT-ESAM increase apical $CAR^{Ex8}$ and AdV transduction.

FIG. 5 shows that $TAT-CAR^{Ex8}$ increases apical $CAR^{Ex8}$ and AdV transduction. (A) Western blotting of MDCK cells treated with either $TAT-CAR^{Ex8}$ or control $TAT-CAR^{Ex8}$-AA. A marked increase in $CAR^{Ex8}$ protein level was seen in the $TAT-CAR^{Ex8}$ treatment but not the mutated peptides. (B) QPCR of the AdV viral genome showed a significant increase in the AdV genomic transduction after $TAT-CAR^{Ex8}$ treatment condition as compared to controls. (C) Polarized MDCK cells were treated with either $TAT-CAR^{Ex8}$ or TAT-ESAM and the apical surface subjected to apical surface biotinylation, followed by neutravidin pull down and Western blot of apical surface proteins. (D) QPCR for AdV viral genome showed a significant increase in the AdV genomic transduction in the $TAT-CAR^{Ex8}$ and TAT-ESAM treatment condition as compared to control. (E) TAT-cell permeable peptides interrupt $MAGI-1-CAR^{Ex8}$ interactions. Western immunoblots showing immunoprecipitates (IP, left lanes) from inducible $MDCK-CAR^{Ex8}$ epithelia pretreated with $TAT-CAR^{Ex8}$ or control $TAT-CAR^{Ex8}$-AA. Stable $MDCK-CAR^{Ex8}$ cells were induced with 200 ng/ml Dox for 24 hrs. After overnight induction, cells were treated with either $TAT-CAR^{Ex8}$ or $TAT-CAR^{Ex8}$-AA (100 μM). $CAR^{Ex8}$ was immunoprecipitated using flag antibody. MAGI-1 was blotted to determine co-IP. Note the marked reduction in MAGI-1 coimmunoprecipitated with $Flag-CAR^{Ex8}$ from MDCK pretreated with $TAT-CAR^{Ex8}$. Right lanes show cell lysate with no immunoprecipitation, acting as positive controls. (F) $TAT-CAR^{Ex8}$ and TAT-ESAM-mediated increase of apical $CAR^{Ex8}$ is reduced by the protein synthesis inhibitor cycloheximide (CHX). Western immunoblotting of $CAR^{Ex8}$ in MDCK epithelia treated with either $TAT-CAR^{Ex8}$ or TAT-ESAM in the presence or absence of the protein synthesis inhibitor CHX. TAT-PDZ3 binding peptides increase $CAR^{Ex8}$ protein level, the effect was reduced upon pretreatment with CHX. *p<0.05.

Figure 6:
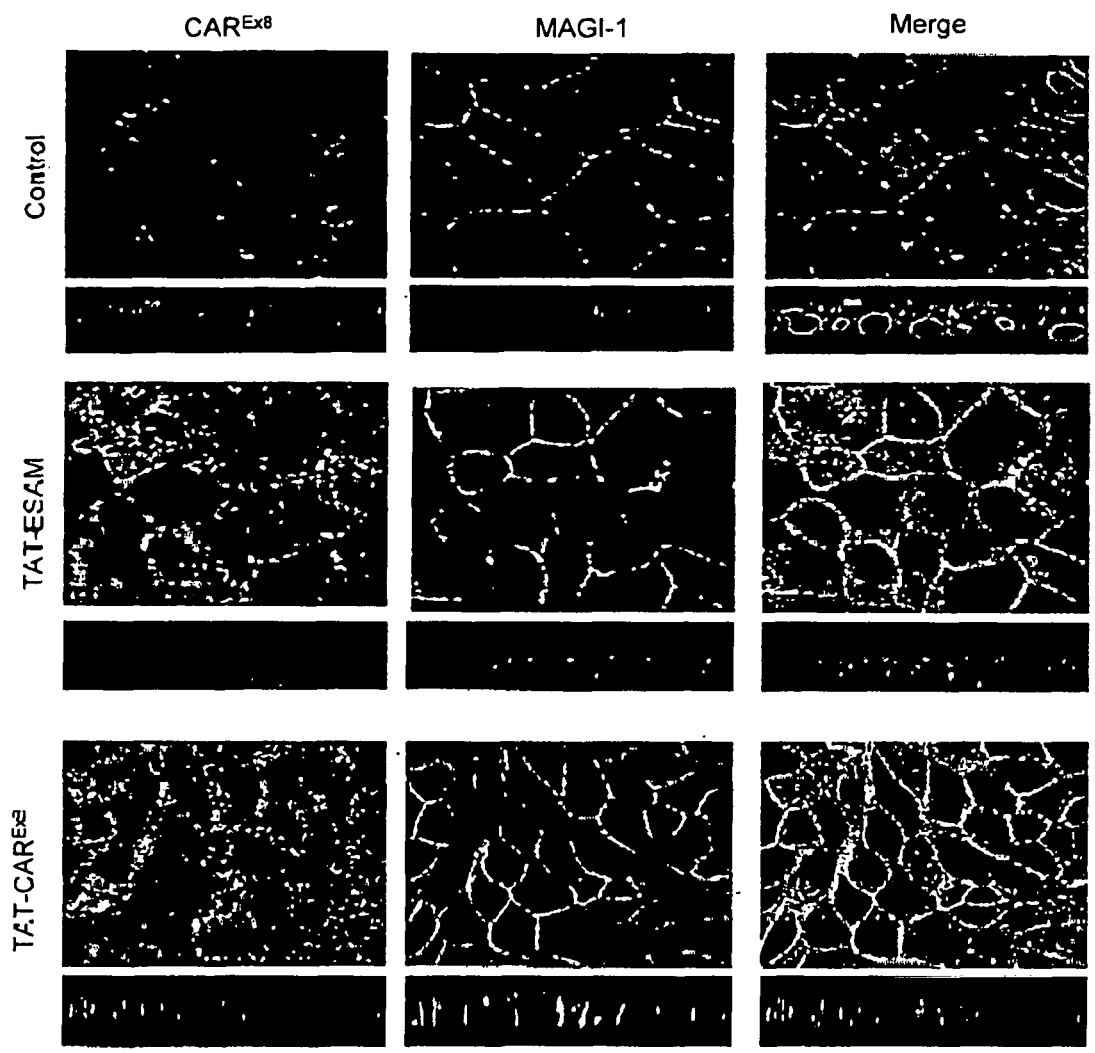
FIG. 6 shows that TAT-PDZ3 binding peptides increase $CAR^{Ex8}$ protein at the apical membrane and in a vesicular pattern within the cytoplasm.

FIG. 6 shows that TAT-PDZ3 peptides increase $CAR^{Ex8}$ protein (red, left column) at the apical membrane and in vesicular pattern within the cytoplasm. Immunocytochemistry of polarized MDCK treated with TAT-ESAM or $TAT-CAR^{Ex8}$ shows upregulation of the cellular $CAR^{Ex8}$ protein level. $CAR^{Ex8}$ is localized mainly at the apical surface of polarized MDCK cells. After treatment with TAT-ESAM or $TAT-CAR^{Ex8}$, $CAR^{Ex8}$ is upregulated in a vesicular pattern within the cytoplasm and at the apical surface of treated cells. Red ($CAR^{Ex8}$), Green (MAGI-1, a junctional protein), Blue (nucleus, DAPI). 60× oil immersion confocal microscopy.

Figure 7:
FIG. 7 shows a significant increase in the AdV genomic transduction in the TAT-$CAR^{Ex8}$ and TAT-ESAM treatment condition as compared to control (PBS) in well differentiated primary human airway epithelia.
Figure 7:
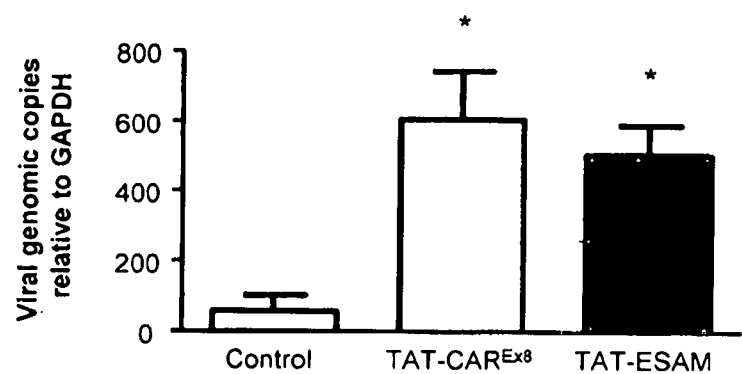

In FIG. 7 shows that PDZ3 binding peptides increase $CAR^{Ex8}$ and adenovirus infection in well differentiated organotypic primary human airway epithelia. Panel (A) shows that polarized human airway epithelial cells treated with either $TAT-CAR^{Ex8}$ or TAT-ESAM and subjected to western blotting for $CAR^{Ex8}$ protein had increased $CAR^{Ex8}$ protein relative to control. Panel (B) shows that qPCR for Ad viral genome showed a significant increase in the AdV genomic transduction in the $TAT-CAR^{Ex8}$ and TAT-ESAM treatment condition as compared to control (PBS). *p<0.05 compared to control.

Figure 8:
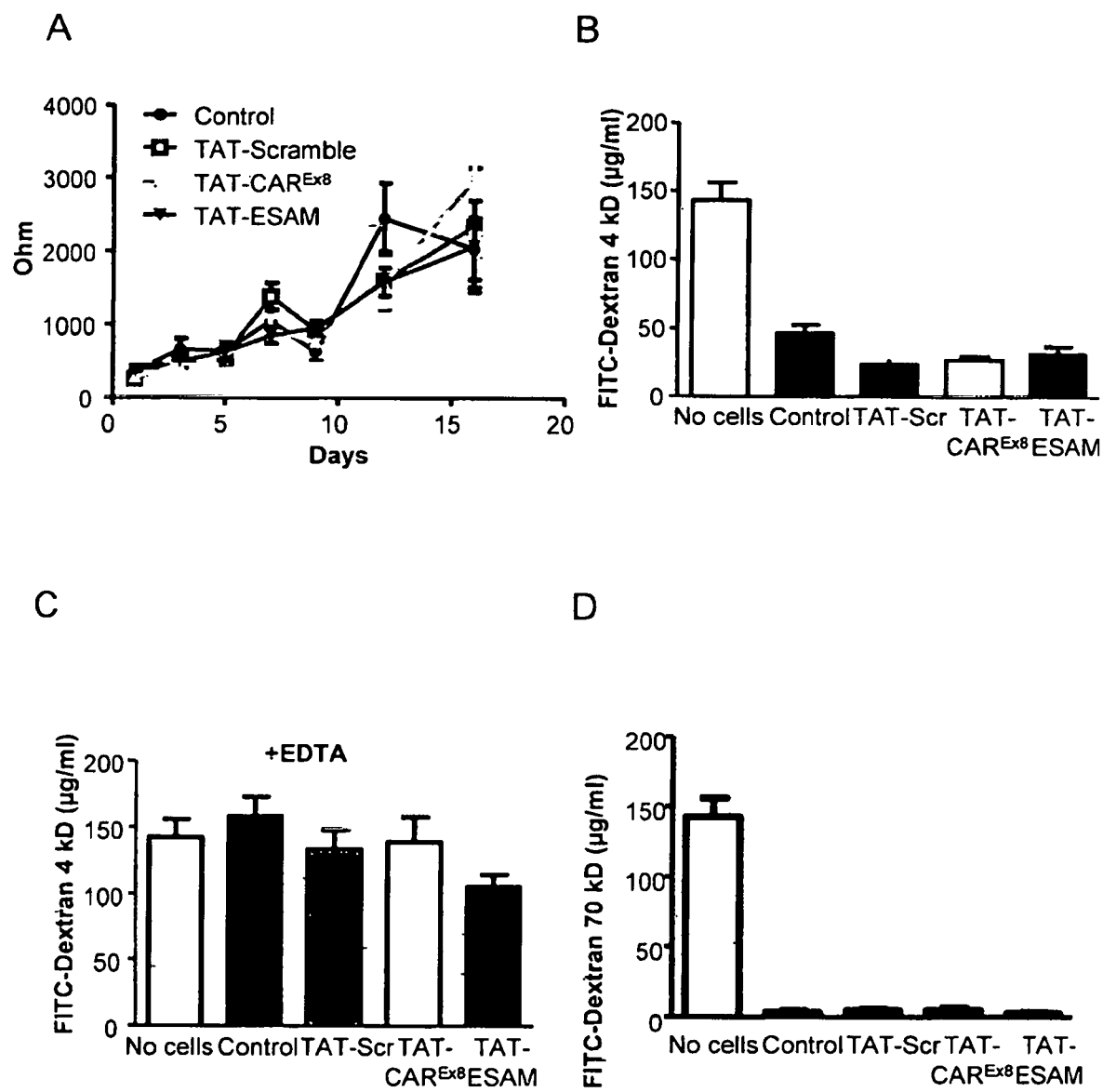
FIG. 8 shows that TAT-PDZ3 peptides (TAT-CAR$^{Ex8}$ and TAT-ESAM) do not change epithelial integrity and are non-toxic to primary human airway epithelia.

FIG. 8 shows that TAT-PDZ3 peptides do not change epithelial integrity. In panel (A), epithelial cells were seeded on transwells and treated with a single dose of PBS, TAT-scramble or TAT-PDZ3 ($TAT-CAR^{Ex8}$ or TAT-ESAM) peptides (50 μM) daily for 16 days. Transepithelial resistance (TER) was measured every other day for 16 days to indicate the amount of epithelial polarization. No difference in TER was noticeable upon treatment with TAT-PDZ3 peptides in comparison to control conditions indicating that polarization was the same in the presence or absence of peptide. Each condition represents the average of 4 replicates. (B) FITC-Dextran 4 kDa diffusion across treated epithelia in the absence of EDTA. There was no difference in Dextran 4 kDa diffusion among treatments indicating that the epithelia tight junctions were intact. (C) Pre-treatment with EDTA to disrupt tight junctions increased Dextran 4 kDa permeability in all conditions. FITC-Dextran 4 kDa was added to the apical membrane compartment and Dextran present in the basolateral media was measured and quantified. (D) There was no difference in FITC-Dextran 70 kDa diffusion across treated epithelia among treatments indicating that the epithelial tight junctions were intact. FITC-Dextran 70 kDa was added to the apical membrane compartment and Dextran in the basolateral media was measured and quantified. Together these data indicate that peptide treatment does not affect epithelial cell growth and polarization, important measures that indicate biology was normal and there was no overt toxicity.

Figure 9:
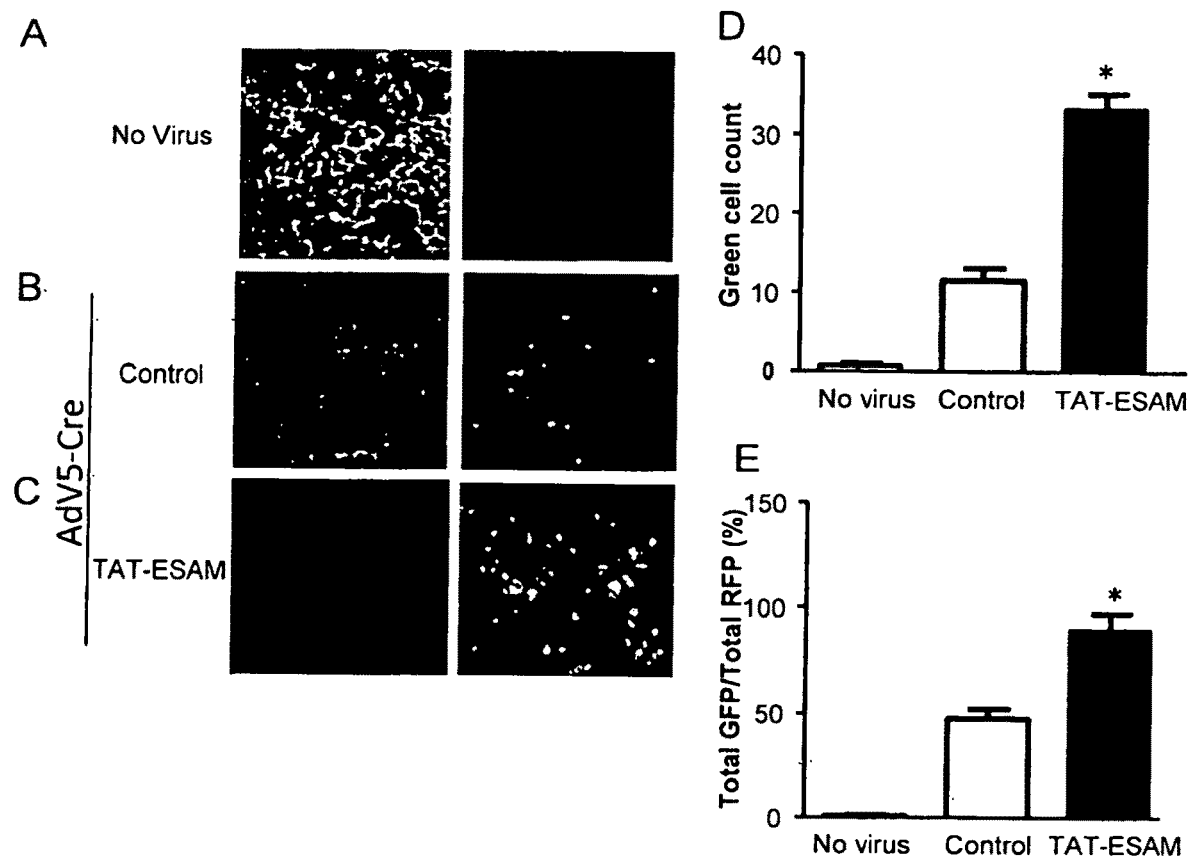
FIG. 9 shows that MAGI-1 PDZ3 binding peptides (TAT-ESAM) increase AdV5-Cre infection in vivo.

FIG. 9 shows that PDZ3 binding peptides increase AdV5-Cre infection in vivo. Analysis of lung cryosections from tdT mice pretreated with A) No virus, B) Control (PBS or $TAT-CAR^{Ex8}$-AA), or C) PDZ3 TAT-ESAM binding peptide 4 h prior to AdV5-Cre intranasal infection. 20× confocal microscopy. (D) Quantitative analysis of GFP expressing cells in lung cryosections from tdT mice with no virus, pre-treated with control, or PDZ3 binding TAT-ESAM peptides. (E) Quantification of total GFP/Total RFP fluorescence in lung section of different treated conditions by image J analysis. There is significantly higher GFP expression in TAT-ESAM treated mice relative to control or uninfected (no virus) conditions. Data are average of quantification from 10 sections. *p<0.05.

Figure 10:
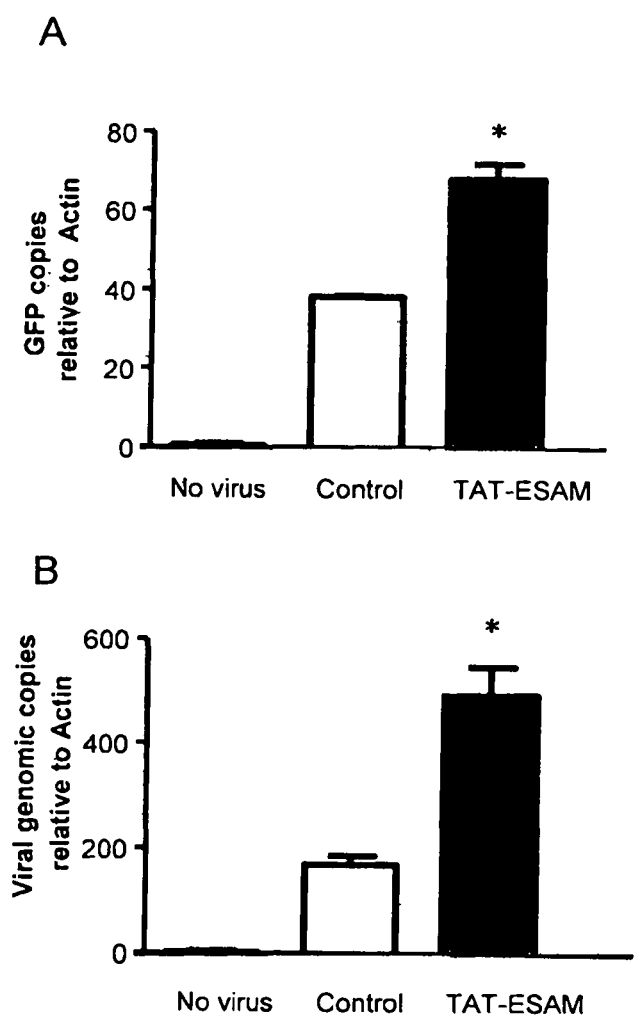
FIG. 10 shows that MAGI-1 PDZ3 binding peptides (TAT-ESAM) increase AdV5-Cre infection in vivo.

FIG. 10 shows that MAGI-1 PDZ3 binding peptides increase AdV5-Cre infection in vivo. (A) Quantitative RT-PCR for GFP mRNA expression after isolation of total RNA from lung tissue of control or peptide treated mice. (B) QPCR of viral genome copies in lung tissue from control or peptide treated mice. There is a significant increase of GFP expression as well as viral genome copies in lung tissue from TAT-PDZ3 treated mice, respectively. *p<0.05.

Figure 11:
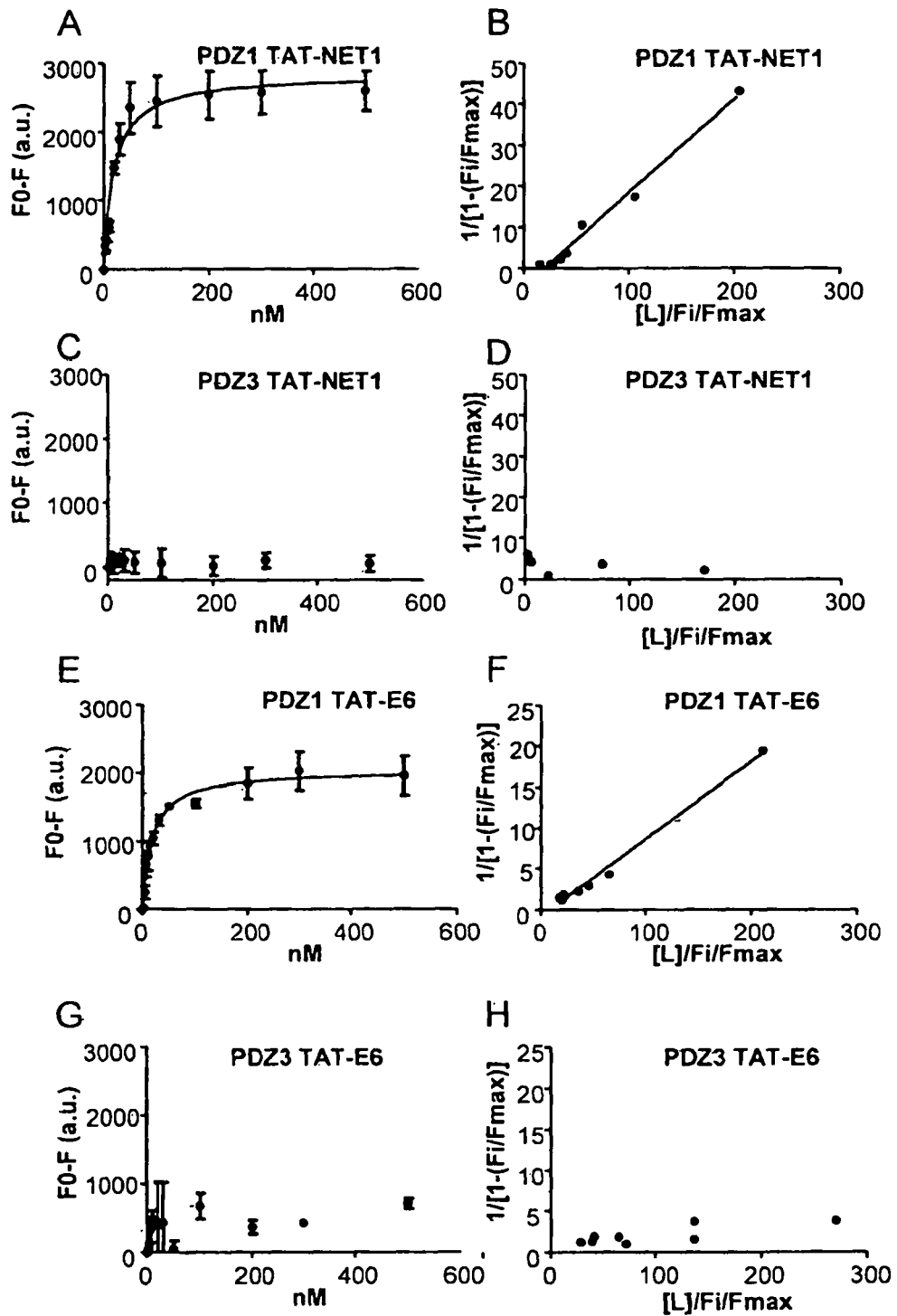
FIG. 11 shows that TAT-PDZ1 binding peptides (TAT-E6 and TAT-NET1) bind selectively to MAGI-1 PDZ1 domain.

FIG. 11 shows that TAT-PDZ1 binding peptides bind selectively to the MAGI-1 PDZ1 domain. Ligand binding assay between TAT-NET1 or TAT-E6 peptide and purified MAGI-PDZ-1. MAGI-1 PDZ3 domain was used as a control. TAT-NET1 binds to MAGI-1 PDZ1 (A, B) but not PDZ3 (C, D) (TAT-NET1 Kd=28±11 nM). Double reciprocal plot (B) showed was linear indicating a single binding site between TAT-NET1 and PDZ1 but not (D) PDZ3 domain. TAT-E6 binds to MAGI-1 PDZ1 (E, F) but not PDZ3 (G, H) (TAT-E6 Kd=15±4 nM). Double reciprocal plot (F) was linear indicating a single binding site between the ligand and PDZ1 but not PDZ3 domain (H).

Figure 12:
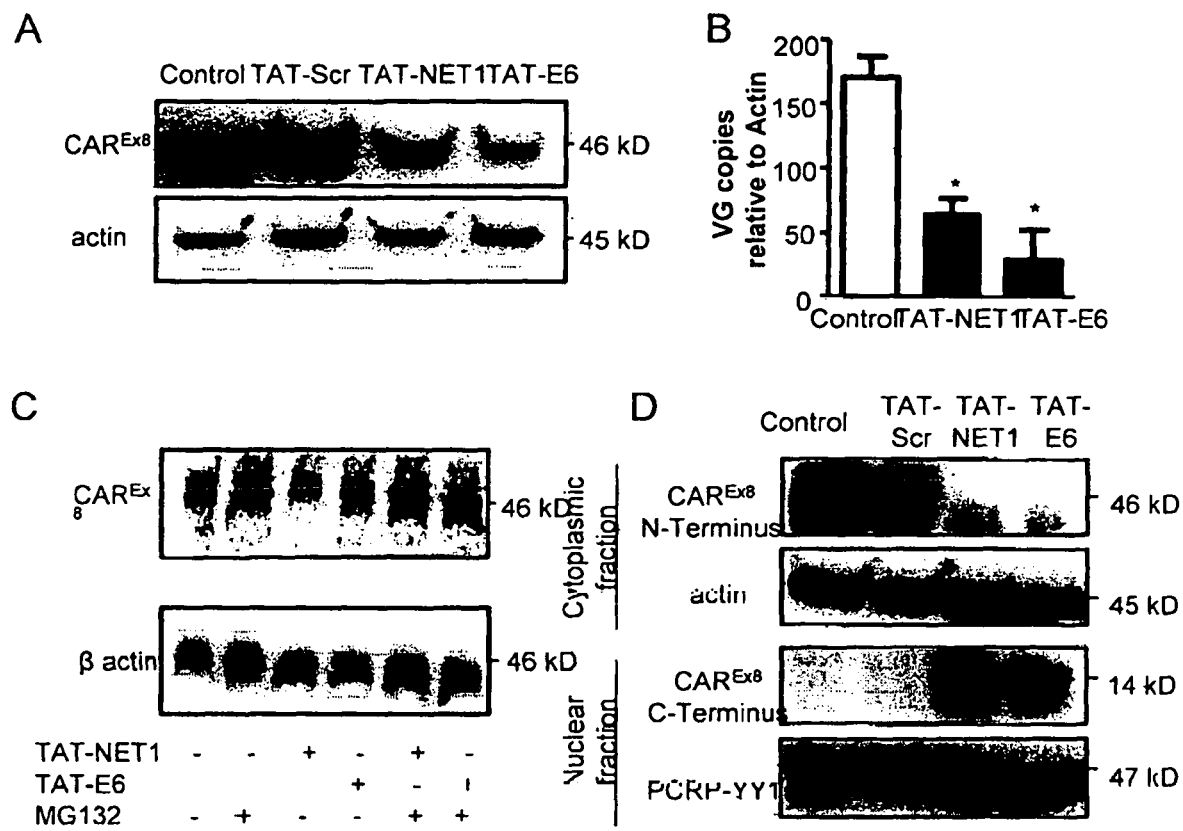
FIG. 12 shows that TAT-PDZ1 binding peptides decrease CAR$^{Ex8}$ protein levels and AdV transduction.

FIG. 12 shows that TAT-PDZ1 binding peptides decrease $CAR^{Ex8}$ protein levels and AdV transduction. (A) Western Blotting from MDCK epithelia treated with either TAT-scramble or TAT-PDZ1 peptides (TAT-E6 or TAT-NET1). A marked decrease in $CAR^{Ex8}$ protein level was seen in the TAT-PDZ1 treated conditions. Actin was used to confirm equal protein loading. (B) QPCR of the AdV viral genome showed a significant decrease in AdV entry into MDCK epithelia treated with the TAT-E6 or TAT-NET1 as compared to control. *p<0.05. (C) TAT-PDZ1 binding peptides decrease $CAR^{Ex8}$ by inducing degradation of the translated protein as shown by Western Blotting of cell lysate from MDCK epithelia treated with TAT-PDZ1 peptides in the presence or absence of the proteosomal and RIP inhibitor, MG-132. Pre-treatment with MG-132 rescued the full length $CAR^{Ex8}$ from TAT-PDZ1 induced degradation. (D) TAT-PDZ1 binding peptides translocate the $CAR^{Ex8}$ cytoplasmic domain to the nucleus. MDCK $CAR^{Ex8}$ cells were induced with 50 ng/ml Dox after which they were treated with 100 µM of TAT-Scr, TAT-NET1, or TAT-E6. Immunoblotting from cellular fractionation of MDCK epithelia into cytoplasmic and nuclear fractions is shown. Treatment with TAT-PDZ1 markedly decreases $CAR^{Ex8}$ in the cellular fraction. A 14 KD band corresponding to the cytoplasmic domain of $CAR^{Ex8}$ was present in the nuclear fraction in the TAT-PDZ1 treated conditions. Actin (cytoplasmic) and PCRP-YY1 (nuclear) were used to confirm equal protein loading in the cytoplasmic and nuclear fraction, respectively.

Figure 13:
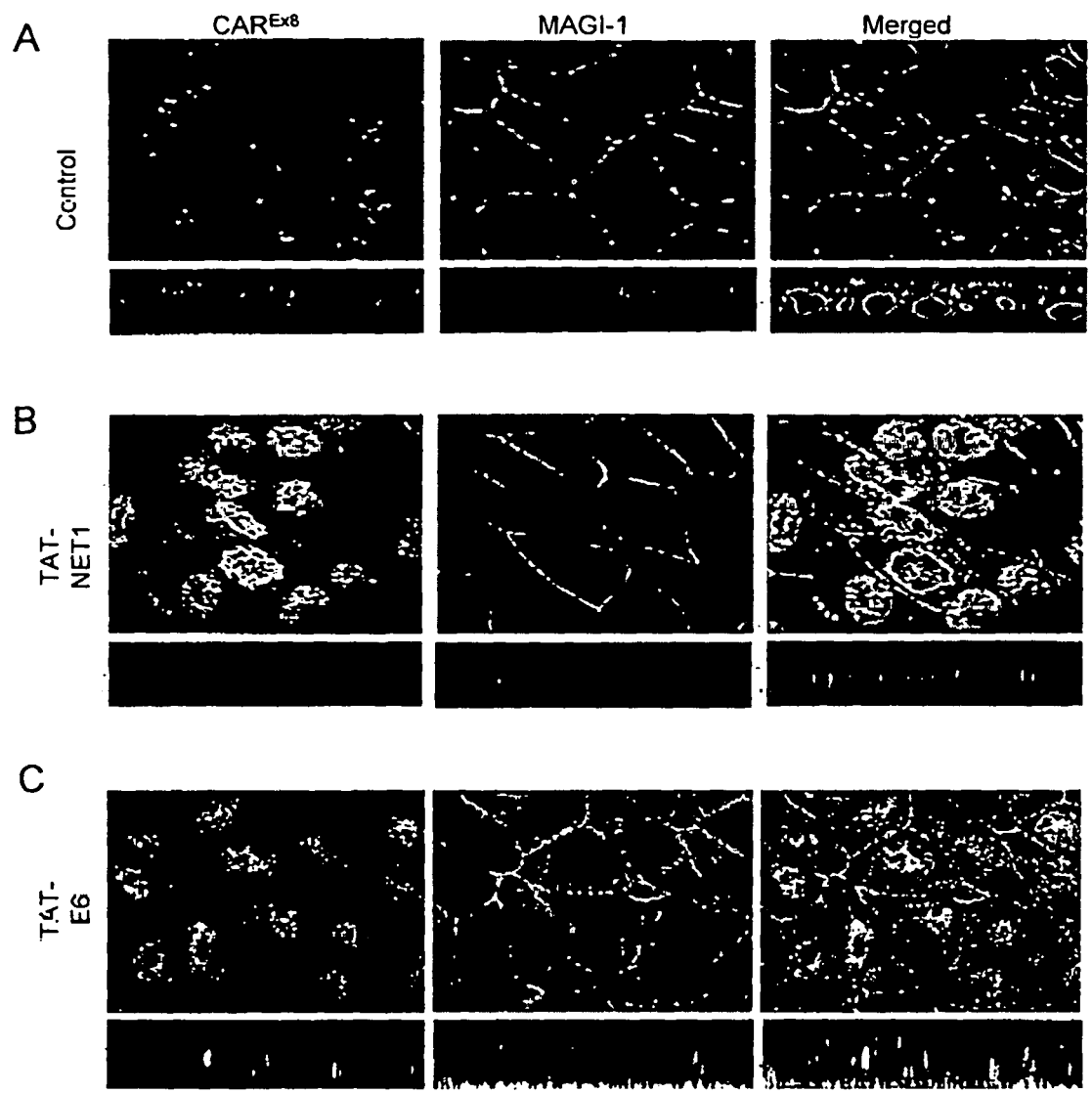
FIG. 13 shows TAT-PDZ1 binding peptides change the immunolocalization of endogenous CAR$^{Ex8}$.

FIG. 13 shows that TAT-PDZ1 binding peptides change the immunolocalization of endogenous $CAR^{Ex8}$. (A) $CAR^{Ex8}$ (red) localizes mainly at the apical membrane of MDCK epithelial cells (see xz section). (B) Treatment with TAT-NET1 (50 µM) or (C) TAT-E6 (50 µM) causes delocalization of $CAR^{Ex8}$ to the nuclear compartment but has minor to no effect on the junctional staining of MAGI-1 (green). 60× oil immersion confocal microscopy.

Figure 14:
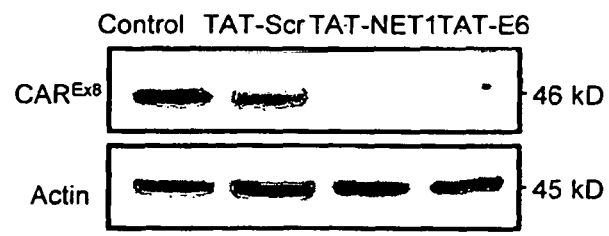
FIG. 14 shows that TAT-PDZ1 binding peptides decreased CAR$^{Ex8}$ protein levels and AdV transduction in well differentiated primary human airway epithelia.
Figure 14:
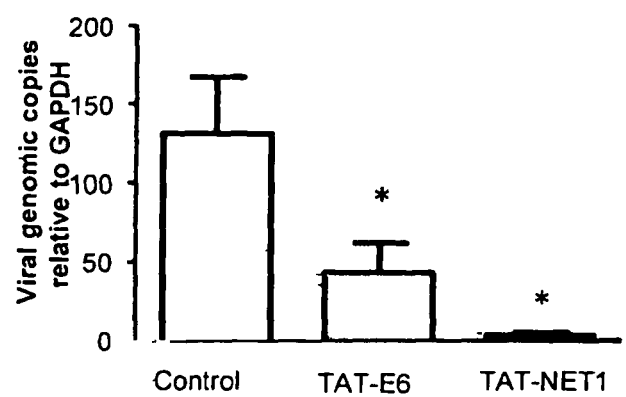

FIG. 14 shows that TAT-PDZ1 binding peptides decrease $CAR^{Ex8}$ protein levels and AdV transduction in well differentiated organotypic primary human airway epithelia. (A) Western blotting from human airway epithelia treated with either TAT-scramble or TAT-PDZ1 peptides (TAT-E6 or TAT-NET1). A marked decrease in $CAR^{Ex8}$ protein level was seen in the TAT-PDZ1 treated conditions. Actin was used to confirm equal protein loading. (B) QPCR of the AdV viral genome showed a significant decrease in AdV entry into HAE treated with the TAT-E6 or TAT-NET1 as compared to control. *p<0.05 versus control.

Figure 15:
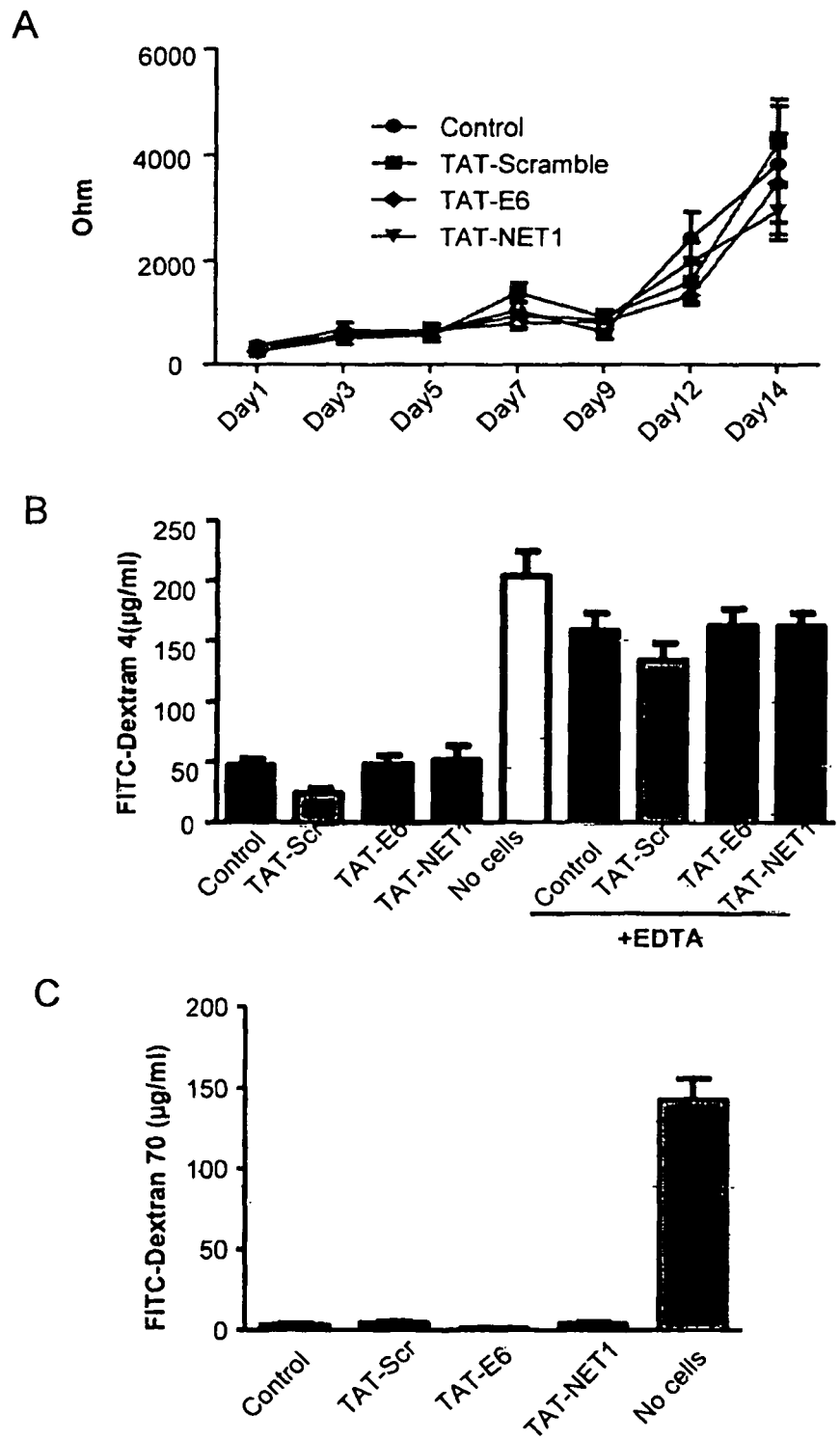
FIG. 15 shows that TAT-PDZ1 peptides do not change epithelial integrity and are non-toxic in primary human airway epithelia.

FIG. 15 shows that TAT-PDZ1 peptides do not change epithelial integrity. (A) Primary human airway epithelial cells were treated with a single dose of PBS, TAT-scramble (50 µM), or TAT-PDZ1 peptides (50 µM) each day for 14 days. Transepithelial resistance (TER) was taken every other day for 14 days. No change in TER was noticeable upon treatment with TAT-PDZ1 peptides indicating similar epithelium formation. (B) FITC-Dextran 4 kDa diffusion across treated epithelia in the presence or absence of EDTA. There was no difference in Dextran 4 kDa diffusion among treatments indicating intact epithelial tight junctions. Pre-treatment with EDTA increased Dextran 4 kDa permeability similarly in all conditions indicating disruption of epithelial tight junctions. FITC-Dextran 4 kDa was added to the apical membrane and the diffused Dextran was collected from the basolateral media and measured. (C) There was no difference in Dextran 70 kDa diffusion among treatments indicating intact epithelial tight junctions. FITC-Dextran 70 kDa was added to the apical membrane and the diffused Dextran was collected from the basolateral media and measured.

Figure 16:
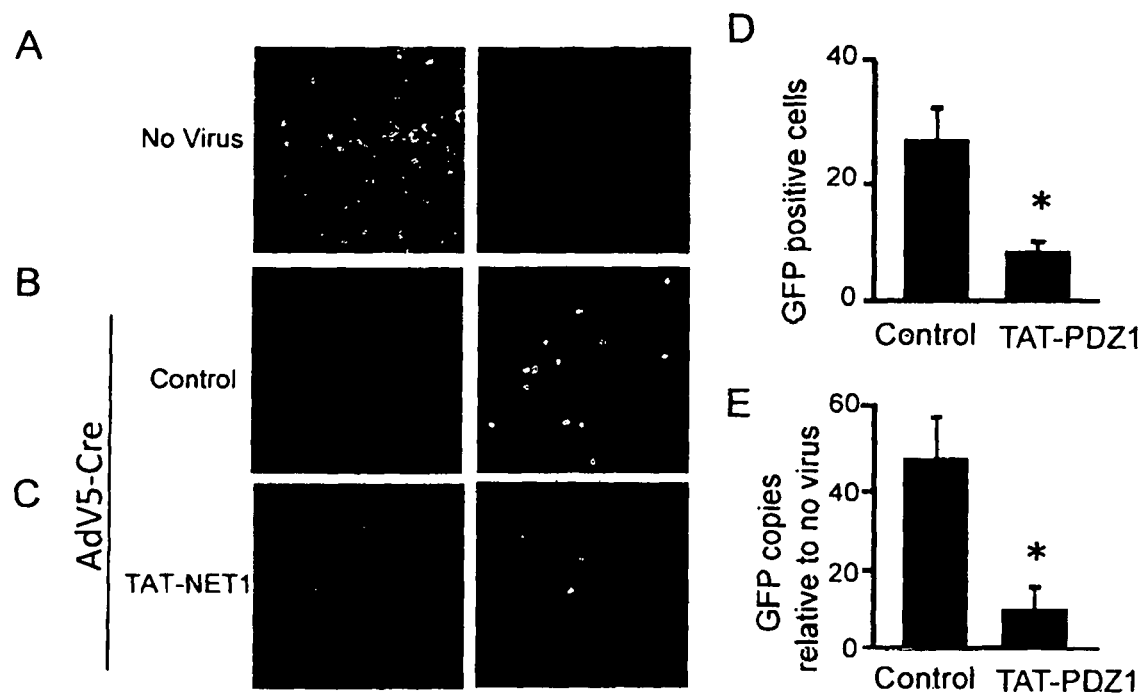
FIG. 16 shows that MAGI-1 PDZ1 binding peptides decrease AdV5-Cre infection in vivo.

FIG. 16 shows that MAGI-1 PDZ1 binding peptides decrease AdV5-Cre infection in vivo. Analysis of lung cryosections from tdT mice pretreated with A) No virus, B) Control (PBS), C) PDZ1 TAT-NET1 binding peptide, 4 h prior to AdV5-Cre intranasal infection in B) and C). 20× confocal microscopy. D) Quantitative analysis of the number of GFP expressing cells in lung cryosections from tdT mice with no virus, pre-treated with control PDZ1 TAT-NET1 peptides. E) Quantification of total GFP/Total RFP fluorescence in lung section of different treated conditions by image J analysis. There is significantly lower GFP expression in TAT-NET1 treated mice. Data are average of quantification from 10 sections. *p<0.05.

Figure 17:
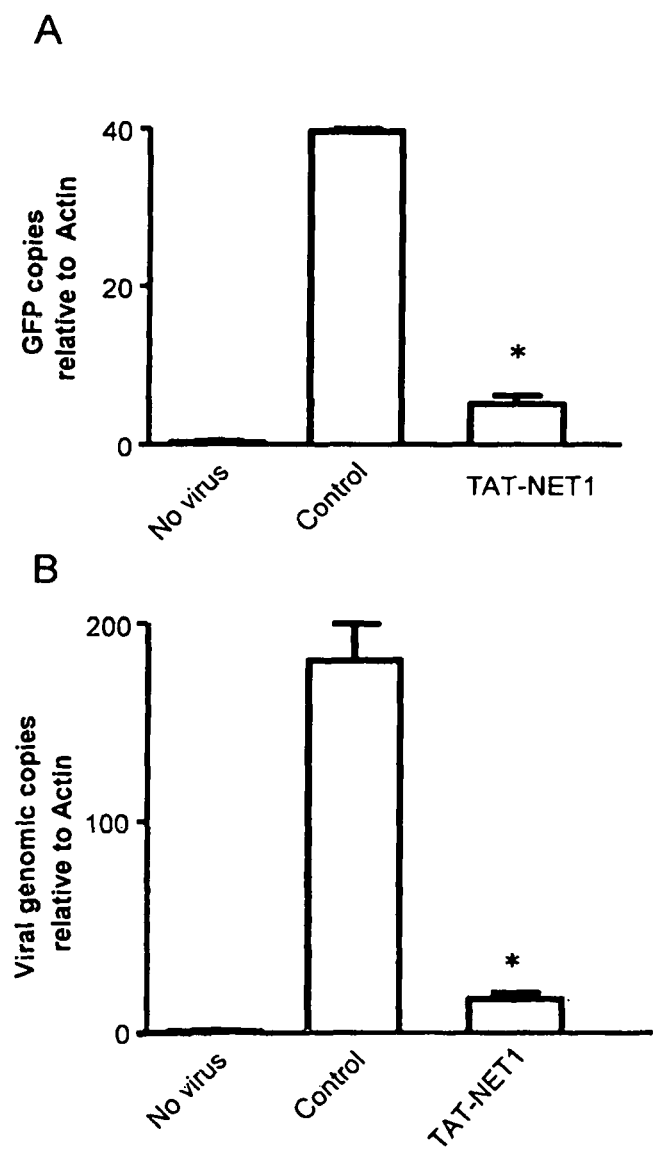
FIG. 17 shows that MAGI-1 PDZ1 binding peptides decrease AdV5-Cre infection in vivo.

FIG. 17 shows that MAGI-1 PDZ1 binding peptides decrease AdV5-Cre infection in vivo. (A) Quantitative RT-PCR for GFP mRNA expression after isolation of total RNA from lung tissue of control or peptide treated mice. (B) QPCR of viral genome copies in lung tissue from control or peptide treated mice. There is a significant decrease of GFP expression as well as viral genome copies in lung tissue from TAT-PDZ3 treated mice. *p<0.05 TAT-NET1 versus Control.

Figure 18:
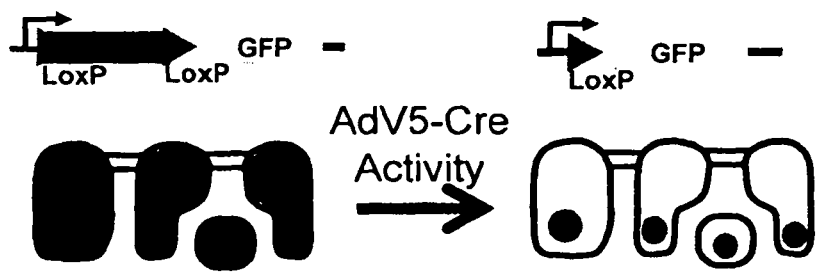
FIG. 18 shows that MAGI-1 PDZ1 binding peptides decrease AdV5-Cre infection whereas MAGI-1 PDZ3 binding peptides increase AdV5-Cre infection in vivo.
Figure 18:
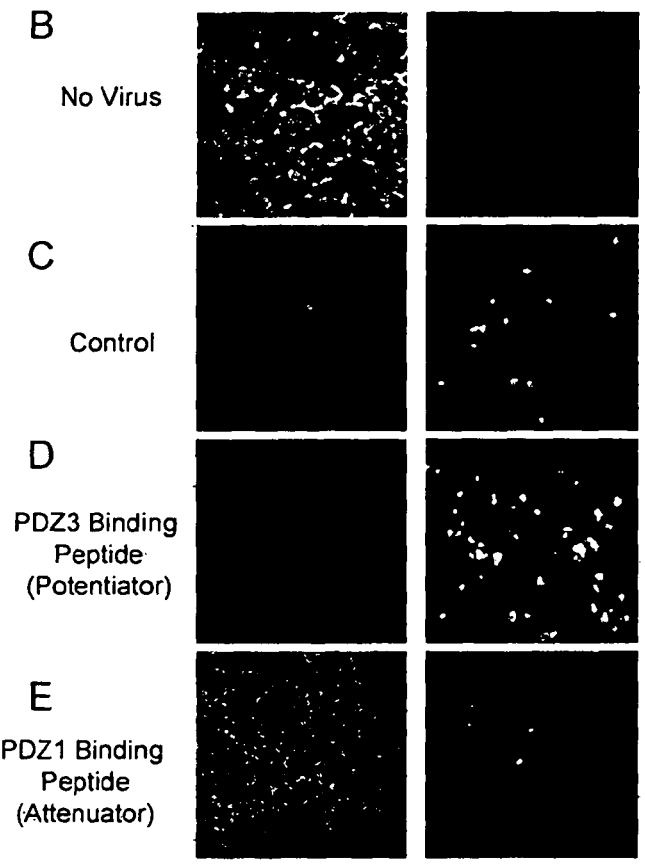
Figure 18:
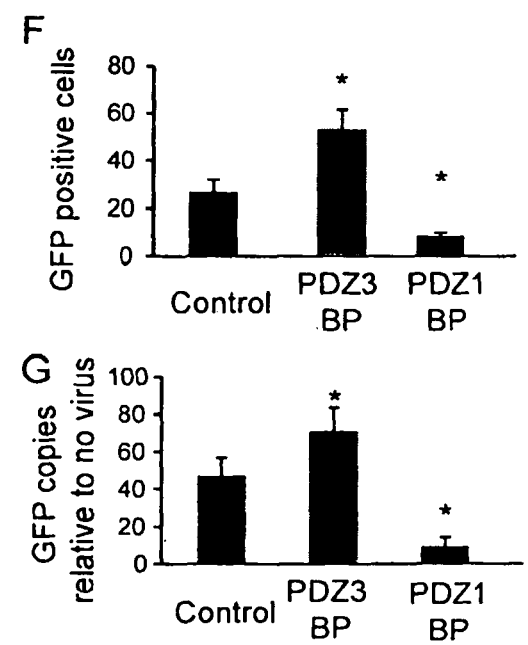

FIG. 18 shows that MAGI-1 PDZ1 binding peptides decrease AdV5-Cre infection whereas MAGI-1 PDZ3 binding peptides increase AdV5-Cre infection in vivo. (A) In tdT tomato mice, all cells contain red fluorescent Tomato protein and fluoresce red. Upon expression of cre recombinase via AdV-Cre infection, infected cells cleave out the tdT gene and express GFP making infected cells fluoresce green. B-E) Lung cryosections from tdT mice pretreated with B) control peptide but no virus infection, C) PBS and AdV5-Cre intranasal infection, D) PDZ3 binding peptide TAT-ESAM and AdV5-Cre intranasal infection, or E) PDZ1 binding peptide TAT-NET1 and AdV5-Cre intranasal infection. F) Quantitation of GFP positive cells per field of view. G) Quantitative RT-PCR for GFP mRNA relative to uninfected tdT mice. Together these data showed increased GFP expression upon TAT-ESAM treatment and decreased GFP expression upon TAT-NET1 treatment as compared to control. *p<0.05 versus control. 20× confocal microscopy.

Figure 19:
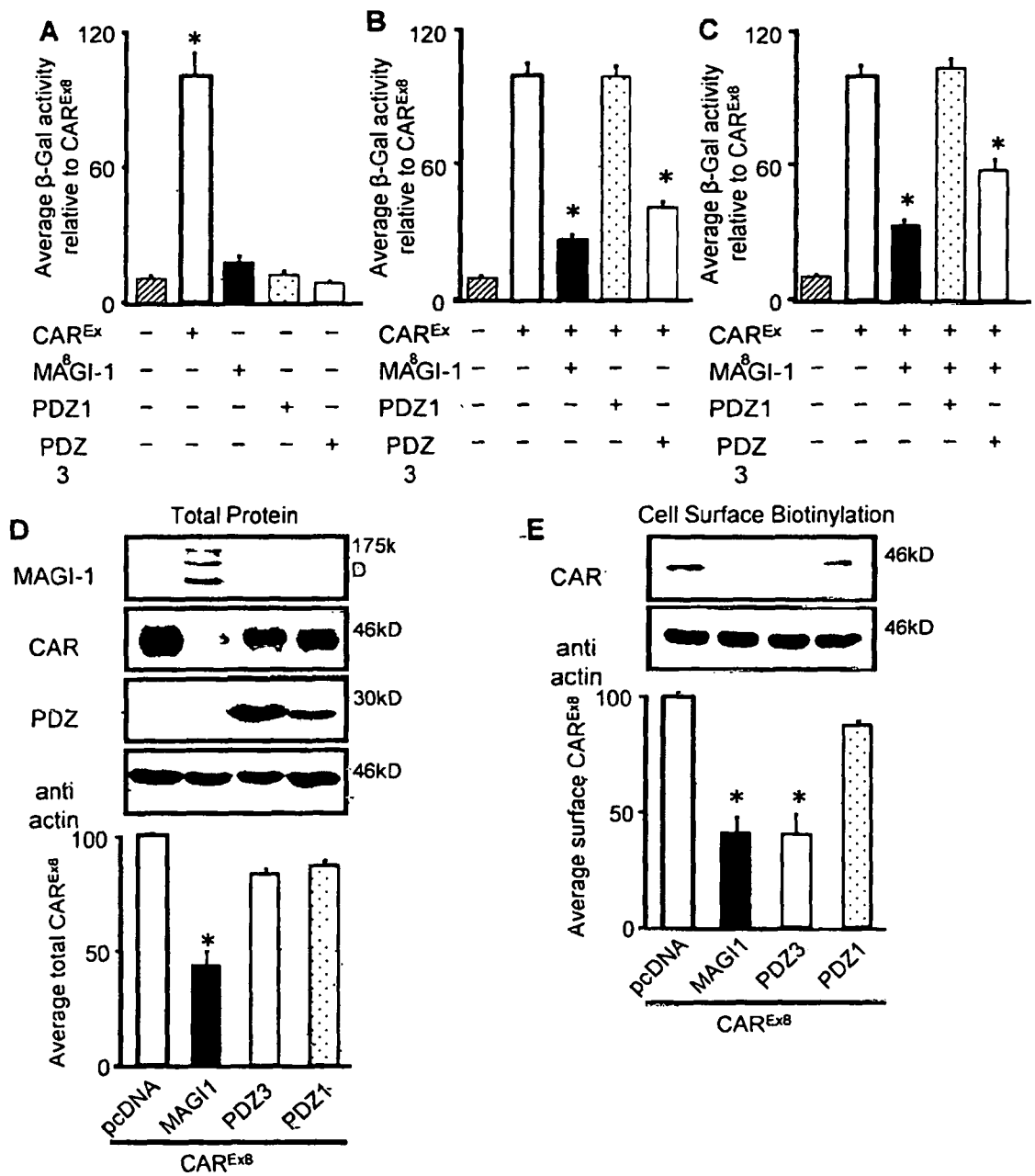
FIG. 19 shows that MAGI-1 PDZ3 decoy domain decreases viral infection, while PDZ1 decoy domain inhibits MAGI-1-mediated CAR$^{Ex8}$ suppression to allow adenovirus infection.

FIG. 19 shows that MAGI-1 PDZ3 domain decreases viral infection, while PDZ1 domain inhibits MAGI-1-mediated $CAR^{Ex8}$ suppression to allow adenovirus infection. CAR-deficient CHO-K1 cells were A) single, B) double, or C) triple transfected with plasmids encoding $CAR^{Ex8}$, MAGI-1 (black bars), PDZ1 domain (dotted bars), or PDZ3 domain (white bars), and balanced with empty pcDNA3.1 plasmid, followed by AdV-β-Gal (MOI 100) transduction. CHO-K1 cells were double transfected with $CAR^{Ex8}$ and pcDNA3.1, MAGI-1, PDZ3, or PDZ1 and analyzed for D) total $CAR^{Ex8}$ protein or E) cell-surface biotinylated $CAR^{Ex8}$ protein expression. Quantification of at least three individual experiments is shown in all bar graphs. *p<0.05.

E. References

1. CHARBONNIER, S, NOMINE Y, RAMIREZ J, LUCK K, CHAPELLE A, SOTE R H, TRAVE G, KEIFFER B, ATKINSON R A, The structural and dynamic response of MAGI-1 PDZ1 with noncanonical domain boundaries to the binding of human papillomavirus E6, J Mol Bio, 2011, pp. 745-63, 406(5).
2. CHASTRE E, ABDESSAMAD M, KRUGLOV A, BRUYNEEL E, BRACKE M, BRACKE M, DI GIOIA Y, BECKERLE M C, VAN ROY F, KOTELEVETS L, TRIP6, a novel molecular partner of the MAGI-1 scaffolding molecule, promotes invasiveness, FASEB J., 2009, pp. 916-28, 23(3).
3. DEV K K, Making protein interactions druggable: targeting PDZ domains, Nat Rev Drug Discov, 2004, pp. 1047-56, 3(12).
4. DOBROSOTSKAYA I Y, JAMES; G L. MAGI-1 interacts with beta-catenin and is associated with cell-cell adhesion structures, Biochem Biophys Res Commun, 2000, pp. 903-9, 270.
5. DOBROSOTSKAYA I Y. Identification of NET1 as a candidate ligand for the first PDZ domain of MAGI-1. Biochem Biophys Res Commun, 2001, pp. 969-75, 283.
6. EXCOFFON K J, KOLAWOLE A O, KUSAMA N, GANSEMER N D, SHARMA P, KRUSKA-HAGEMAN A M, PETROFF E, BENSON C J, Coxsackievirus and adenovirus receptor (CAR) mediates trafficking of acid-sensing ion channel 3 (ASIC3) via PSD-95. Biochem Biophys Res Commun, 2012, pp. 13-18, 425. PMID: 22809504.
7. EXCOFFON, KJDA, BOWERS, J B AND SHARMA P, Alternative Splicing of Viral Receptors: A Review of the Diverse Morphologies and Physiologies of Adenoviral Receptors. Recent Research Developments in Virology. In Press.
8. EXCOFFON KJDA, GANSEMER N D, MOBILY M E, KARP P H, PAREKH K R, ZABNER J, Isoform-specific regulation and localization of the Coxsackie and adenovirus receptor in human airway epithelia, PLoS One, 2010, p. e9909, 5(3). PMID: 2845650.
9. EXCOFFON, KJDA, HRUSKA-HAGEMAN, A, KLOTZ, M, TRAVER, G AND ZABNER J, A role for the PDZ binding domain of the Coxsackie B virus and Adenovirus Receptor (CAR) in cell adhesion and growth, J Cell Sci, 2004, pp. 4401-9, 117(Pt 19). PMID: 15304526.
10. GLAUNSINGER B A, LEE S S, THOMAS M. BANKS L, JAVIER R, Interactions of the PDZ-protein MAGI-1 with adenovirus E4-ORF1 and high-risk papillomavirus E6 oncoproteins, Oncogene, 2000, pp. 5270-80, 19.
11. H E J, BELLINI M, INUZUKA H, X U J, XIONG Y, YANG X, CASTLEBERRY A M, HALL R A, Proteomic analysis of beta1-adrenergic receptor interactions with PDZ scaffold proteins, J Biol Chem, 2006, pp. 2820-7, 281.
12. HIRABAYASHI S, TAJIMA M, YAO I, NISHIMURA, MORI H, HATA Y, JAM4, a junctional cell adhesion molecule interacting with a tight junction protein MAGI-1, Mol Cell Biol, 2003, pp. 4267-82, 23. PMID: 156145.
13. HIRABAYASHI S, MORI H, KANSAKU A, KURIHARA H, SAKAI T, SHIMIZU F, KAWACHI H, HATA Y, MAGI-1 is a component of the glomerular slit diaphragm that is tightly associated with nephrin, Lab Invest, 2005, pp. 1528-43, 85.
14. LEE C. LAIMINS L, A Role of the PDZ domain-binding motif of the oncoprotein E6 in the pathogenesis of human papillomavirus type 31, J Virol, 2004, pp. 12366-77, 78(22).
15. KOLAWOLE A O, SHARMA P, YAN R, LEWIS K J, HOSTETLER H A, ASHBOURNE EXCOFFON K J. The PDZ1 and PDZ3 Domains of MAGI-1 Regulate the Eight Exon Isoform of the Coxsackievirus and Adenovirus Receptor, J Virol, 2012, pp. 9244-54, 86(17). PMID: 22718816, PMID: 3416107.
16. KOTELEVETS L, VAN HENGEL J, BRUYNEEL E, MAREEL M, VAN ROY F, CHASTRE E, Implication of the MAGI-1b/PTEN signalosome in stabilization of adherens junctions and suppression of invasiveness, FASEB J, 2005, pp. 115-7, 19.
17. KUMAR M, LIU H, RICE A P, Regulation of interferon-β by MAGI-1 and its interaction with influenza A virus NS1 protein with ESEV PBM, PLOS One, 2012, p. e41251, 7(7).
18. MINO A, OHTSUKA T, INOUE E, TAKAI Y, Membrane-associated guanylate kinase with inverted orientation (MAGI)-1/brain angiogenesis inhibitor 1-associated protein (BAP1) as a scaffolding molecule for Rap small G protein GDP/GTP exchange protein at tight junctions, Genes Cells, 2000, pp. 1009-16, 5.
19. OHNO H, HIRABAYASHI S, KANSAKU A, YAO I, TAJIMA M, NISHIMURA W, OHNISHI H, MASHIMA H, FUJITA T, OMATA M, HATA Y, Carom: a novel membrane-associated guanylate kinase-interacting protein with two SH3 domains, Oncogene, 2003, pp. 8422-31, 22.
20. PATRIE K M, DRESCHER A J, GOYAL M, WIGGINS R C, MARGOLIS B, The membrane-associated guanylate kinase protein MAGI-1 binds megalin and is present in glomerular podocytes, J Am Soc Nephrol, 2001, pp. 667-77, 12.
21. PATRIE K M, DRESCHER A J, WELIHINDA A, MUNDEL P, MARGOLIS B, Interaction of two actin-binding proteins, synaptopodin and alpha-actinin-4, with the tight junction protein MAGI-1, J Biol Chem, 2002, pp. 30183-90, 277.
22. RIDGWAY L D, KIM E Y, DRYER S E, MAGI-1 interacts with Slo1 channel proteins and suppresses Slo1 expression on the cell surface, Am J Physiol Cell Physiol, 2009, pp. C55-65, 297.

23. SHARMA P, KOLAWOLE A O, CORE S B, KAJON A K, EXCOFFON KJDA, Sidestream Smoke Exposure Increases the Susceptibility of Airway Epithelia to Adenoviral Infection, PLoS One, 2012, p. e49930, 7(11). PMID: 23166798.
24. SHARMA P, KOLAWOLE A O, WILTSHIRE S M, FRONDORF K, EXCOFFON KJDA, Accessibility of the coxsackievirus and adenovirus receptor (CAR) and its importance in adenovirus gene transduction efficiency, Journal of General Virology, 2011, pp. 155-8, EPub. PMID: 21918008.
25. SHIRATSUCHI T, ODA K, NISHIMORI H, SUZUKI M, TAKAHASHI E, TOKINO T, NAKAMURA Y, Cloning and characterization of BAP3 (BAI-associated protein 3), a C2 domain-containing protein that interacts with BAI1, Biochem Biophys Res Commun, 1998, pp. 158-65, 251.
26. TANEMOTO M, TOYOHARA T, ABE T, ITO S, MAGI-1a functions as a scaffolding protein for the distal renal tubular basolateral K+ channels, J Biol Chem, 2008, pp. 12241-7, 283.
27. THOMAS M, KRANJEC C, NAGASAKA K, MATLASHEWSKI G, BANKS L, Analysis of the PDZ binding specificities of Influenza A virus NS1 proteins, Virol J, 2011, p. 25, 8. PMID: 3030508.
28. WEGMANN F, EBNET K, DU PASQUIER L, VESTWEBER D. BUTZ S, Endothelial adhesion molecule ESAM binds directly to the multidomain adaptor MAGI-1 and recruits it to cell contacts, Exp Cell Res, 2004, pp. 121-33, 300.
29. ZHANG Y, DASGUPTA J, MA R Z, BANKS L., THOMAS M, CHEN X S, Structures of a human papillomavirus (HPV) E6 polypeptide bound to MAGUK proteins: mechanisms of targeting tumor suppressors by a high-risk HPV oncoprotein, J Virol, 2007, pp. 3618-26, 81. PMID: 1866053.

F. Tables

TABLE 1

| Protein (Gene) | Sequence | MAGI-1 PDZ domain | SEQ ID No |
|---|---|---|---|
| Potential Potentiators | | | |
| ESAM | AQSQAGSLV | 3 | 21 |
| Slo1a (KCNMA1) | QKYVQEERL | 3 | 22 |
| Slo1b (KCNMA1) | QNRKEMVYR | 3 | 23 |
| Slo1c (KCNMA1) | PIREVEDEC | 3 | 24 |
| CAR$^{Ex7}$ | AQSKDGSIV | 3 | 25 |
| Nephrin | LPFELRGHLV | 2, 3 | 26 |
| BAI-1 | QDIIDLQTEV | 3, 4 | 27 |
| CAR$^{Ex8}$ | YKTDGITVV | 1, 3 | 28 |
| Ad9 E4Orf1 | PSVKIATLV | 1, 3 | 29 |
| Potential Attenuators | | | |
| NET1 | GGKKKETLV | 1 | 30 |
| Beta1AR (ADRB1) | PGFASESKV | 1 | 31 |
| HPV E6 | SRTRRETQL | 1 | 32 |
| RapGEP | DEDEQVSAV | 0, 1 | 33 |
| Influenza A virus NS1 | MARTARSKV | 1, 5 | 34 |
| JAM4 | QKVRNVTLV | 1, 4 | 35 |

(single letter amino acid code)

TABLE 2

(single letter amino acid code)

| Cell-penetrating peptide | Sequence | SEQ ID NO: |
|---|---|---|
| Tat | GRKKRRQRRRPPQ | 1 |
| AP/Penetratin | RQIKIWFQNRRMKWKK | 2 |
| Poly-arginine | RRRRRRRR | 3 |
| Sim2 | AKAARQAAR | 4 |
| VP22 | DAATATRGRSAASRPTERPRAPARSASRPRRVD | 5 |
| pVEC | LLIILRRRIRKQAHAHSK-amide | 6 |
| pISL | RVIRVWFQNKRCKDKK-amide | 7 |
| hCT (9-32) derived peptide | LGTYTQDFNKFHTFPQTAIGVGAP | 8 |
| LL-37 | LLGDFFRKSKEKIGKEFKRIVQRIKDFLRNLVPRTES | 9 |
| Mouse PrP (1-28) | MANLGYWLLALFVTMWTDVGLCKKRPKP-amide | 10 |

TABLE 2-continued (single letter amino acid code)

| Cell-penetrating peptide | Sequence | SEQ ID NO: |
|---|---|---|
| Transportan (TP) | GVVTLNSAGYLLGKINLKALAALAKKIL-amide | 11 |
| TP10 | AGYLLGKINLKALAALAKKIL-amide | 12 |
| Arg11 | RRRRRRRRRRR | 13 |
| MAP | KLALKLALKALKAALKLA-amide | 14 |
| Pep-1 | KETWWETWWTEWSQPKKKRKV | 15 |
| Pep-2 | KETWFETVVFTEWSQPKKKRKV | 16 |
| MPG | GALFLGWLGAAGSTMGAPKKKRKV | 17 |
| KALA | WEAKLAKALAKALAKHLAKALAKALKACEA | 18 |
| ppTG1 | GLFKALLKLLKSLWKLLLKA | 19 |
| ppTG20 | GLFRALLRLLRSLWRLLLRAS | 20 |

TABLE 3

Summary of human adenoviruses

| Subgroup | Types | Disease | Receptor |
|---|---|---|---|
| A | 12, 18, 31 | Respiratory Meningoencephalitis | CAR |
| B1 | 16, 21, 35, 50 | Respiratory, Cystitis | CD46 |
| B2 | 3, 7, 14 | Pharyngo-conjunctivitis | DSG2 |
| B3 | 11 | | CD46, DSG2 |
| B | 34, 55 | | ? |
| C | 1, 2, 5, 6, 57 | Respiratory, Hepatitis | CAR |
| D | 8-10, 13, 15, 17, 19, 20, 22-30, 32, 33, 36-39, 42-49, 51, 53, 54, 56 | Keratoconjunctivitis | CAR |
| E | 4 | Respiratory | CAR |
| F | 40, 41 | Gastroenteritis | CAR |
| G | 52 | Gastroenteritis | CAR |

What is claimed:

1. A method of decreasing apical surface localization of coxsackievirus and adenovirus receptors ("CAR") in a target cell comprising the step of: exposing the target cell to a composition comprising a peptide, wherein said peptide comprises (i) a first peptide portion having a first peptide comprising SEQ ID NO: 2 and (ii) a second peptide portion having a second peptide sequence comprising SEQ ID NO: 32, thereby decreasing apical surface localization of CAR in the target cell.

2. The method of claim 1, wherein the second peptide portion having the first peptide sequence consisting of SEQ ID NO: 2 and the second peptide sequence consisting of 32.

3. A method of reducing CAR-mediated viral infection comprising the step of: decreasing apical surface localization of CAR in an infected target cell, wherein the decreasing apical surface localization of CAR is achieved by exposing the infected target cell to a composition comprising a peptide, wherein said peptide comprises (i) a first peptide portion having a first peptide SEQ ID NO: 2 and (ii) a second peptide portion having a second peptide sequence comprising SEQ ID NO: 32, thereby decreasing apical surface localization of CAR in the target cell.

4. A method of protecting a target cell from CAR mediated viral infection comprising the step of: decreasing apical surface localization of CAR in a target cell to be protected, wherein the decreasing apical surface localization of CAR is achieved by (i) exposing the target cell to be protected to a composition comprising a first peptide, wherein said first peptide comprises (i) a first peptide portion having a first peptide sequence comprising SEQ ID NO: 2 and (ii) a second peptide portion having a second peptide sequence comprising SEQ ID NO: 32, thereby decreasing apical surface localization of CAR in the target cell and thereby protecting the target cell from CAR mediated viral infection.

5. A method of protecting a target cell from CAR mediated viral infection of claim 4, wherein the first peptide consisting of SEQ ID NO: 2 and the second peptide sequence consisting of SEQ ID NO: 32, thereby modulating an apical surface localization of CAR in the target cell.

6. A composition for modulating CAR expression on cells, the composition comprising: a peptide that comprises first and second portions, the first portion (i) comprising a cell penetrating peptide and the second portion (ii), the second portion (ii) comprising the peptide of SEQ ID NO: 32.

7. A composition of claim 6, comprising a peptide, wherein said peptide comprises (i) a first peptide portion having a first peptide sequence comprising SEQ ID NO: 2 and (ii) a second peptide portion having a second peptide sequence comprising SEQ ID NO: 32.

8. The composition according to claim 6, wherein (i) is a peptide having a sequence that has a sequence consisting of SEQ ID NO: 2.

9. The composition according to claim 6, wherein (ii) is a peptide having a sequence that has a sequence consisting of SEQ ID NO: 32.

10. The composition according to claim 6, wherein (i) is a peptide having a sequence that has a sequence consign of SEQ ID NO: 2 and (ii) a second peptide portion having a second peptide sequence consisting SEQ ID NO: 32.

\* \* \* \* \*